(12) United States Patent
Zhang et al.

(10) Patent No.: US 9,161,990 B2
(45) Date of Patent: Oct. 20, 2015

(54) HYDROCHLORIDE SALTS OF A GLYCOPEPTIDE-CEPHALOSPORIN ANTBIOTIC COMPOND

(71) Applicant: THERAVANCE BIOPHARMA ANTIBIOTICS IP, LLC, South San Francisco, CA (US)

(72) Inventors: Weijiang Zhang, Concord, CA (US); Ronnie Cheung, Redwood City, CA (US); Dimitar Filipov, San Francisco, CA (US); Jack Green, Redwood City, CA (US); Junning Lee, El Granada, CA (US)

(73) Assignee: Theravance Biopharma Antibiotics IP, LLC, South San Francisco, CA (US)

( * ) Notice: Subject to any disclaimer, the term of this patent is extended or adjusted under 35 U.S.C. 154(b) by 0 days.

(21) Appl. No.: 14/198,956

(22) Filed: Mar. 6, 2014

(65) Prior Publication Data

US 2014/0274877 A1    Sep. 18, 2014

Related U.S. Application Data

(60) Provisional application No. 61/779,065, filed on Mar. 13, 2013.

(51) Int. Cl.
| | |
|---|---|
| C07K 9/00 | (2006.01) |
| C07D 498/04 | (2006.01) |
| C07D 519/00 | (2006.01) |
| A61K 47/48 | (2006.01) |
| A61K 38/14 | (2006.01) |

(52) U.S. Cl.
CPC ........... *A61K 47/48246* (2013.01); *A61K 38/14* (2013.01); *C07D 498/04* (2013.01); *C07D 519/00* (2013.01); *C07K 9/008* (2013.01)

(58) Field of Classification Search
None
See application file for complete search history.

(56) References Cited

U.S. PATENT DOCUMENTS

| | | | | |
|---|---|---|---|---|
| 4,258,041 | A | 3/1981 | O'Callaghan et al. | |
| 4,626,534 | A | 12/1986 | Fites et al. | |
| 5,254,545 | A | 10/1993 | Ishibashi et al. | |
| 6,974,797 | B2 * | 12/2005 | Fatheree et al. | 514/2.4 |
| 7,531,623 | B2 | 5/2009 | Liu et al. | |
| 7,601,690 | B2 * | 10/2009 | Fatheree et al. | 514/1.1 |
| 7,649,080 | B2 * | 1/2010 | Fatheree et al. | 530/333 |
| 7,655,621 | B2 * | 2/2010 | Fatheree et al. | 514/1.1 |
| 7,713,931 | B2 * | 5/2010 | Fatheree et al. | 514/1.1 |
| 8,003,755 | B2 | 8/2011 | Liu et al. | |

(Continued)

FOREIGN PATENT DOCUMENTS

| | | |
|---|---|---|
| EP | 0325112 A1 | 1/1989 |
| EP | 0438747 A1 | 12/1990 |

(Continued)

OTHER PUBLICATIONS

Tyrrell et al. In vitro activity of TD-1792, a multivalent glycopeptide-cephalosporin antibiotic, against 377 strains of anaerobic bacteria and 34 strains of Corynebacterium species. Antimicrobial Agents and Chemotherapy (published online Jan. 30, 2012), 56(4), 2194-2197. Available at: http://aac.asm.org/content/56/4/2194.full.pdf.*

(Continued)

*Primary Examiner* — Maury Audet
(74) *Attorney, Agent, or Firm* — Jeffrey A. Hagenah

(57) ABSTRACT

The present invention relates to a compound of formula I:

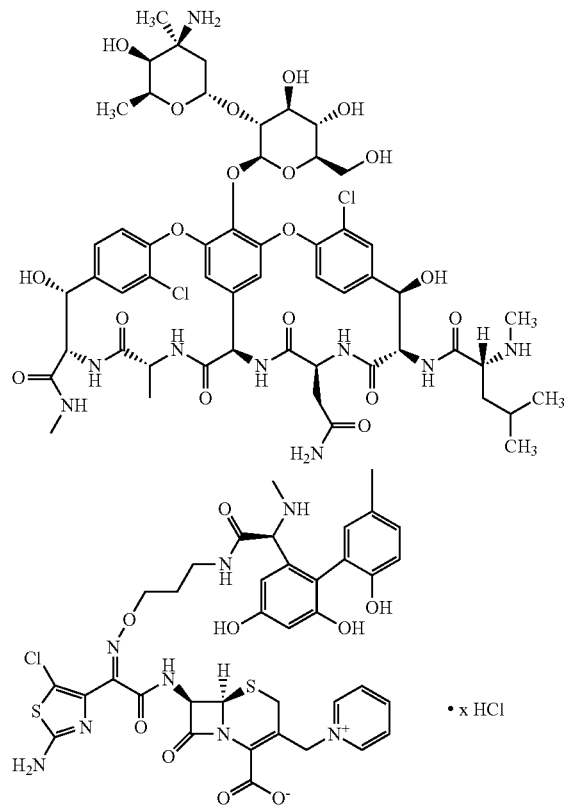

wherein x is in the range of from about 1 to about 2. The invention also relates to pharmaceutical compositions containing such compounds; processes for preparing such compounds; and methods of using such compounds to, for example, treat a bacterial infection.

15 Claims, 3 Drawing Sheets

(56) References Cited

U.S. PATENT DOCUMENTS

| | | |
|---|---|---|
| 2008/0032962 A1 | 2/2008 | Heubes et al. |
| 2008/0103121 A1 | 5/2008 | Gole et al. |
| 2008/0194464 A1 | 8/2008 | Fatheree et al. |
| 2010/0160278 A1 | 6/2010 | Heubes et al. |
| 2011/0124551 A1 | 5/2011 | Palepu et al. |
| 2011/0172167 A1 | 7/2011 | Palepu et al. |

FOREIGN PATENT DOCUMENTS

| | | |
|---|---|---|
| JP | 4142149 B2 | 8/2008 |
| JP | 03/031449 A | 5/2010 |
| WO | 2004/092183 A2 | 10/2004 |
| WO | 2005/042568 A2 | 5/2005 |

OTHER PUBLICATIONS

Blais et al. Antistaphylococcal activity of TD-1792, a multivalent glycopeptide-cephalosporin antibiotic. Antimicrobial Agents and Chemotherapy (published online Dec. 27, 2011), 56(3),1584-1587. Available at: http://aac.asm.org/content/56/3/1584.full.pdf.*
Hedge et al. Pharmacodynamics of TD-1792, a novel glycopeptide-cephalosporin heterodimer antibiotic used against gram-positive bacteria, in a neutropenic murine thigh model. Antimicrobial Agents and Chemotherapy (published online Dec. 12, 2011), 56(3),1578-1583. Available at: http://www.ncbi.nlm.nih.gov/pmc/articles/PMC3294954/pdf/zac1578.pdf.*
The International Search Report and the Written Opinion for PCT/US2014/021064 dated Jun. 10, 2014.
Arakawa et al., "Biotechnology applications of amino acids in protein purification and formulations", Amino Acids, 33: 587-605 (2007).
Blais et al., "Antistaphylococcal activity of TD-1792, a multivalent glycopeptide-cephalosporin antibiotic", Antimicrobial Agents and Chemotherapy, 56(3): 1584-1587 (2012).
Botta et al., "Experimental and theoretical investigations on the cephalosporin delta3-delta2 isomerization", Electronic Journal of Theoretical Chemistry, 1: 52-59 (1996).
Burgess et al., "The Carbohydrate-catalysed hydrolysis of cephalosporins", J. Chem. Soc. Perkin Trans 2: 97-101 (1994).
Carpenter et al., "Comparison of solute-induced protein stabilization in aqueous solution and in the frozen and dried states", J Dairy Sci, 73: 3627-3636 (1990).
Chang et al., "Development of an efficient single-step freeze-drying cycle for protein formulations", Pharmaceutical Research, 12(6): 831-837 (1995).
Chang et al., "Development of a stable freeze-dried formulation of recombinant human interleukin-I receptor antagonist", Pharmaceutical Research, 13(2): 243-249 (1996).
Cocker et al., "Cephalosporanic Acids. Part IV. 7-acylamidoceph-2-2m-4-carboxylic acids", J. Chem. Soc. (C) 1142-1151 (1966).
Diana et al., "Development and validation of an improved method for the analysis of vancomycin by liquid chromatography. Selectivity of reversed-phase columns towards vancomycin components", Journal of Chromatography A, 996: 115-131 (2003).
Hegde et al., "Pharmacodynamics of TD-1792, a novel glycopeptide-cephalosporin heterodimer antibiotic used against gram-positive bacteria, in a neutropenic murine thigh model", Antimicrobial Agents and Chemotherapy, 56(3): 1578-1583 (2012).
Just et al., "Biochemical effects and zonal heterogeneity of peroxisome proliferation induced by periluorocarboxylic acids in rat liver", Hepatology, 9(4): 570-581 (1989).
Kasraian et al., "Characterization of the sucrose/glycine/water system by differential scanning calorimetry and freeze-drying microscopy", Pharmaceutical Development and Technology, 3(2): 233-239 (1998).
Leuthner et al., "In vitro activity of the new multivalent glycopeptide-cephalosporin antibiotic TD-1792 against vancomycin-nonsusceptible staphylococcus isolates", Antimicrobial Agents and Chemotherapy, 54(9): 3799-3803 (2010).
Liu et al., "Freeze-drying of proteins from a sucrose-glycine excipient system: effect of formulation composition on the initial recovery of protein activity", AAPS PharmSci Tech, 6(2): E150-E157 (2005).
Liu, "Freeze-drying, Pharmaceuticals", Encyclopedia of Industrial Biotechnology, pp. 1-18 (2010).
Long et al., "A Multivalent approach to drug discovery for novel antibiotics", J. Antibiotics, 61(10): 595-602 (2008).
Long et al., "Exploring the positional attachment of glycopeptide/B-lactam heterodimers", J. Antibiotics, 61(10): 603-614 (2008).
Meyer et al., "Impact of bulking agents on the stability of a lyophilized monoclonal antibody", European Journal of Pharmaceutical Sciences, 38: 29-38 (2009).
Oguchi et al., "Freeze-drying of drug-additive binary systems. IV. Effects of saccharide addition on the crystallization of cefazolin sodium in frozen aqueous solution", Pharmaceutica Acta helvetiae, 70: 113-116 (1995).
Saab et al., "Isomerization of cephalosporin esters: Implications for the prodrug ester approach to enhancing the oral bioavailabilities of cephalosporins", Journal of Pharmaceutical Sciences, 77(10): 906-907 (1988).
Tyrrell et al., "In vitro activity of TD-1792, a multivalent glycopeptide-cephalosporin antibiotic, against 377 strains of anaerobic bacteria and 34 strains of corynebacterium species", Antimicrobial Agents and Chemotherapy, 56(4): 2194-2197 (2012).
Wang, "Lyophilization and development of solid protein pharmaceuticals", International Journal of Pharmaceutics, 203: 1-60 (2000).

* cited by examiner

HYDROCHLORIDE SALTS OF A GLYCOPEPTIDE-CEPHALOSPORIN ANTBIOTIC COMPOND

CROSS-REFERENCE TO RELATED APPLICATIONS

This application claims the benefit of U.S. Provisional Application No. 61/779,065, filed on Mar. 13, 2013; the entire disclosure of which is incorporated herein by reference in its entirety.

BACKGROUND OF THE INVENTION

1. Field of the Invention

The present invention relates to novel hydrochloride salts of a cross-linked glycopeptide-cephalosporin antibiotic compound and to pharmaceutical compositions containing such hydrochloride salts. This invention also relates to processes for preparing, and methods of using, such hydrochloride salts and compositions.

2. State of the Art

Cross-linked glycopeptide-cephalosporin antibiotics are known in the art. For example, such antibiotics are disclosed in U.S. Pat. Nos. 6,878,868 B2; 6,974,797 B2; 7,067,481 B2; 7,067,482 B2; 7,601,690 B2; and in Long et al., *J. Antibiot.* 61(10): 595-602 (2008); and Long et al., *J. Antibiot.* 61(10): 603-614 (2008). These antibiotics are reported to be useful for treating Gram-positive bacterial infections, including methicillin-resistant *Staphylococci aureus* (MRSA) infections. See, for example, Leuthner et al., *Antimicrob. Agents Chemother.* 2010, 54(9):3799; Hegde et al., *Antimicrob. Agents Chemother.* 2012, 56(3):1578; Blais et al., *Antimicrob. Agents Chemother.* 2012, 56(3):1584; and Tyrell et al., *Antimicrob. Agents Chemother.* 2012, 56(4):2194.

One such cross-linked glycopeptide-cephalosporin antibiotic is 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]-carbonyl]-26-decarboxyvancomycin, which has the chemical structure:

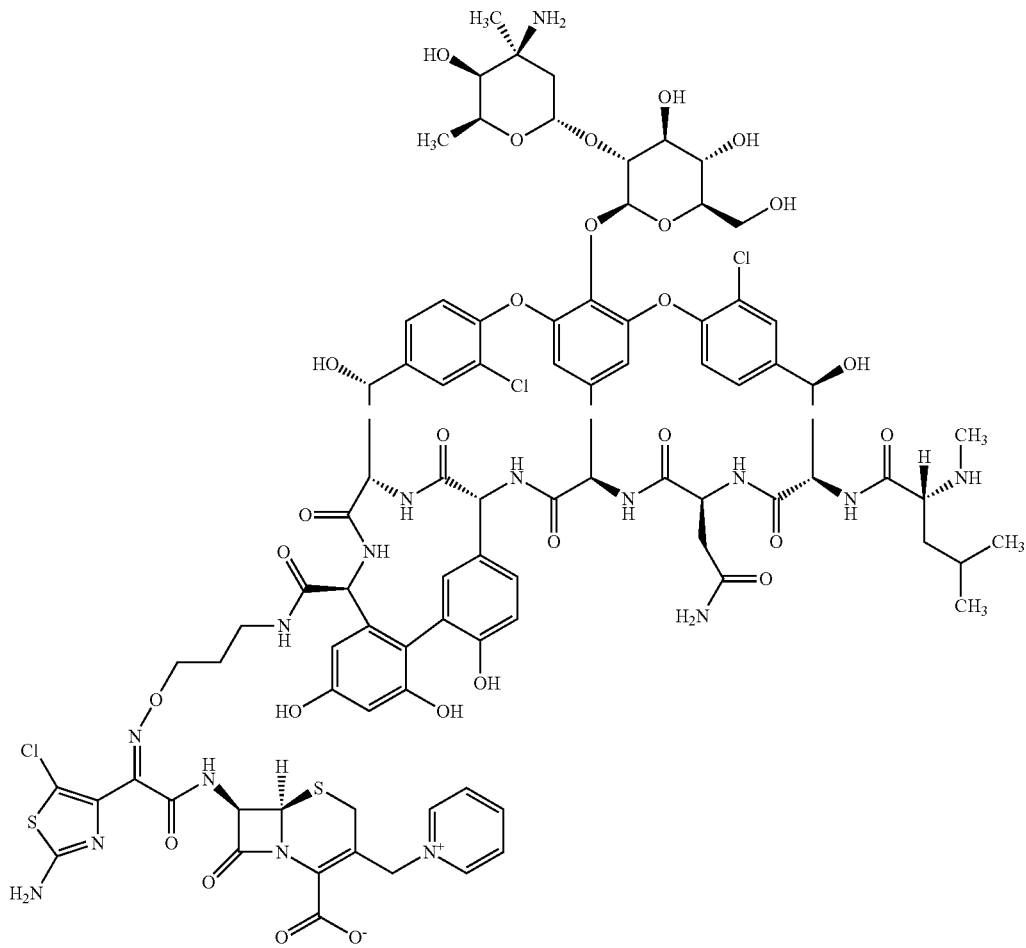

This compound, also known as TD-1792, has been disclosed previously as either a tri(trifluoroacetic acid) salt or a trihydrochloride salt. See, for example, U.S. Pat. No. 6,974,797 B2 at column 34, line 60, to column 35, line 20. The disclosed salt forms, however, have several disadvantages.

First, perfluorocarboxylic acids, such as trifluoroacetic acid, have been reported to produce adverse hepatic effects when administered to rats. See, for example, Just et al., *Hepatology*, 9(4), 570-581 (1989). Therefore, a trifluoroacetic acid salt of this compound may not be pharmaceutically-acceptable for administration to patients.

Additionally, the trihydrochloride salt of this compound has been found to decompose significantly when stored at room temperature or even at refrigerated temperature (about 2 to about 8° C.). Therefore, the trihydrochloride salt may not be acceptable for use in a commercial formulation since pharmaceutical formulations are often stored for significant periods of time prior to use.

Accordingly, a need exists for new pharmaceutically-acceptable salt forms of this compound that have improved storage stability.

Also of interest are new pharmaceutical compositions containing such salts. Of particular interest are new pharmaceutical compositions that further improve the storage stability of the compound. The existing scientific literature, however, is often contradictory with regard to which excipients are useful for providing increased storage stability for pharmaceutical agents.

For example, EP 0 325 112 A1 teaches that cephalosporins are stabilized by dissolving the cephalosporin with lactose, glucose, sucrose or galactose (and optionally, glycine), and then drying the solution.

In contrast, U.S. Pat. No. 5,254,545 teaches that the pharmaceutical preparations of EP 0 325 112 A1 are not satisfactory to stabilize a particular cephalosporin compound and instead the cephalosporin is formulated with (i) lactose, (ii) citric acid or a sodium salt thereof and (iii) arginine or a hydrochloride thereof or sodium chloride to provide a stable preparation.

Moreover, with regard to the use of carbohydrates, Burgess et al., *J. Chem. Soc. Perkin Trans.* 2, 97 (1994) teaches that the decomposition of certain cephalosporins is catalyzed by glucose, galactose, maltose, sucrose, mannitol and α-methylglucoside in aqueous solutions at pH 9-11.

More recently, U.S. Patent Application Publication No. US 2010/010278 A1 discusses the advantages and disadvantages of various excipients used to prepare freeze-dried formulations of cephalosporins, such as polyols and amino acids (page 1, paragraphs 004 to 0019), and concludes that the scientific literature is contradictory and does not make it possible to predict which formulations will provide stability for the freeze-dried product (page 1, paragraph 0020). This document describes freeze-dried formulations for cephalosporin derivatives containing at least one stabilizer selected from carbohydrates, polyhydric alcohols and polyvinyl pyrrolidone.

With regard to pharmaceutical compositions for glycopeptides, EP 0 438 747 A1 discloses stabilized freeze-dried compositions of glycopeptides, such as orienticins A to D, chloroorienticins A to E, and vancomycin, comprising 0.05 parts by weight or more of one or more saccharides.

JP 414249 B2 discloses freeze-dried preparations of vancomycin comprising amino acids selected from arginine, alanine, aspartic acid, histidine and glycine.

Additionally, JP 2010105965 A discloses preparations of vancomycin containing water-soluble acid amides, such as nicotinamide.

Thus, a wide variety of excipients have been disclosed for use in formulating cephalosporins and glycopeptides. The scientific literature, however, is often contradictory as to which excipient to use with a particular pharmaceutical agent. As a result, identifying an excipient or combinations of excipients that improves the storage stability of a cross-linked cephalosporin-glycopeptide is particularly challenging since such compounds contain both cephalosporin and glycopeptide moieties in the same molecule.

SUMMARY OF THE INVENTION

The present invention provides a compound of formula I:

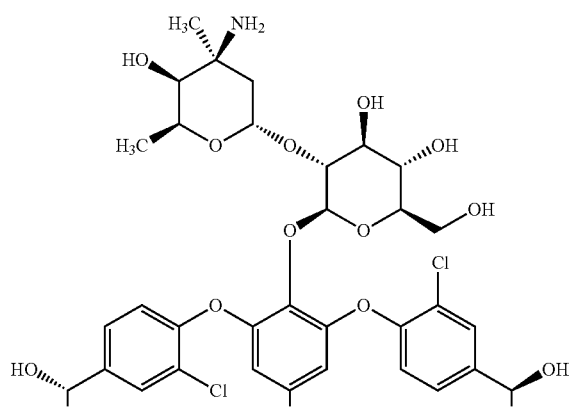

I

-continued

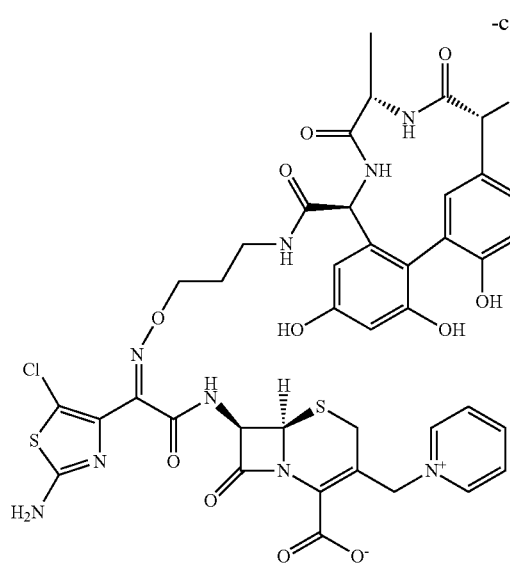
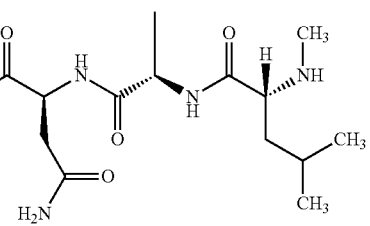

wherein x is in the range of from about 1 to about 2.

Such hydrochloride salts have been discovered to have significantly improved storage stability at room temperature and at refrigerated temperature compared to the corresponding trihydrochloride salt. Additionally, the storage stability of such hydrochloride salts has been found to be further improved in compositions containing sucrose and glycine.

In one embodiment, x is about 1, i.e., the compound of formula I is a monohydrochloride salt. In another embodiment, x is about 2, i.e., the compound of formula I is a dihydrochloride salt.

In another aspect, the present invention provides a pharmaceutical composition comprising a compound of formula I. In one embodiment, the pharmaceutical composition comprises a pharmaceutically acceptable carrier and a compound of formula I. In a particular embodiment, the pharmaceutical composition contains sucrose and glycine.

In yet another embodiment, the pharmaceutical composition comprises:
  (a) a compound of formula I;
  (b) about 0.5 to about 2.0 parts by weight of sucrose; and
  (c) about 0.5 to about 2.0 parts by weight of glycine (as the free base equivalent);
wherein the parts by weight of sucrose and glycine are based on the part by weight of the compound of formula I (as the free base equivalent).

In a particular embodiment, the pharmaceutical composition is a lyophilized composition. In another particular embodiment, the pharmaceutical composition comprises about 1.0 part by weight of sucrose; and about 1.5 parts by weight of glycine. In yet another particular embodiment, the change in purity of the compound of formula I in the pharmaceutical composition is less than about 10% as measured by high performance liquid chromatography after storage for 12 months at a temperature in the range of from about 18° C. to about 25° C.

In another aspect, the present invention provides a method for treating a bacterial infection in a patient using a compound of formula I. In one embodiment, the method comprises administering to the patient a compound of formula I. In another embodiment, the method comprises administering to the patient a pharmaceutical composition comprising a pharmaceutically-acceptable carrier and a compound of formula I.

In another aspect, the present invention provides a compound of formula I for use in therapy. In one embodiment, the use in therapy is for treating a bacterial infection.

In another aspect, the present invention provides a compound of formula I for use in the manufacture of a medicament. In one embodiment, the medicament is for treating a bacterial infection.

In another aspect, the present invention provides a process for preparing a compound of formula I. In one embodiment, the process comprises the steps of:
  (a) forming an aqueous composition comprising 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]-carbonyl]-26-decarboxyvancomycin and hydrochloric acid in a molar ratio of about 1:1 to about 1:2;
  (b) lyophilizing the aqueous composition to provide a compound of formula I.

In another aspect, the present invention provides a product produced by a process described herein.

In another aspect, the present invention provides a method for reducing the degradation of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]-amino]oxy]propyl]amino]-carbonyl]-26-decarboxyvancomycin during storage. In one embodiment, the method comprises (a) forming a compound of formula I and (b) storing the compound of formula I at a temperature in the range of from about −25° C. to about 25° C. In another embodiment, the compound of formula I is stored at about 2° C. to about 8° C.

In yet another embodiment, the method comprises storing a pharmaceutical composition comprising (a) a compound of formula I; (b) about 0.5 to about 2.0 parts by weight of sucrose; and (c) about 0.5 to about 2.0 parts by weight of glycine (as the free base equivalent); wherein the parts by weight of sucrose and glycine are per part by weight of the compound of formula I (as the free base equivalent), at a temperature in the range of from about −25° C. to about 25° C. In another embodiment, the pharmaceutical composition is stored at about 2° C. to about 8° C.

Other aspects and embodiments of this invention are disclosed herein.

BRIEF DESCRIPTION OF THE DRAWINGS

Various aspects of the present invention are illustrated by reference to the accompanying drawings.

DETAILED DESCRIPTION OF THE INVENTION

Figure 1:
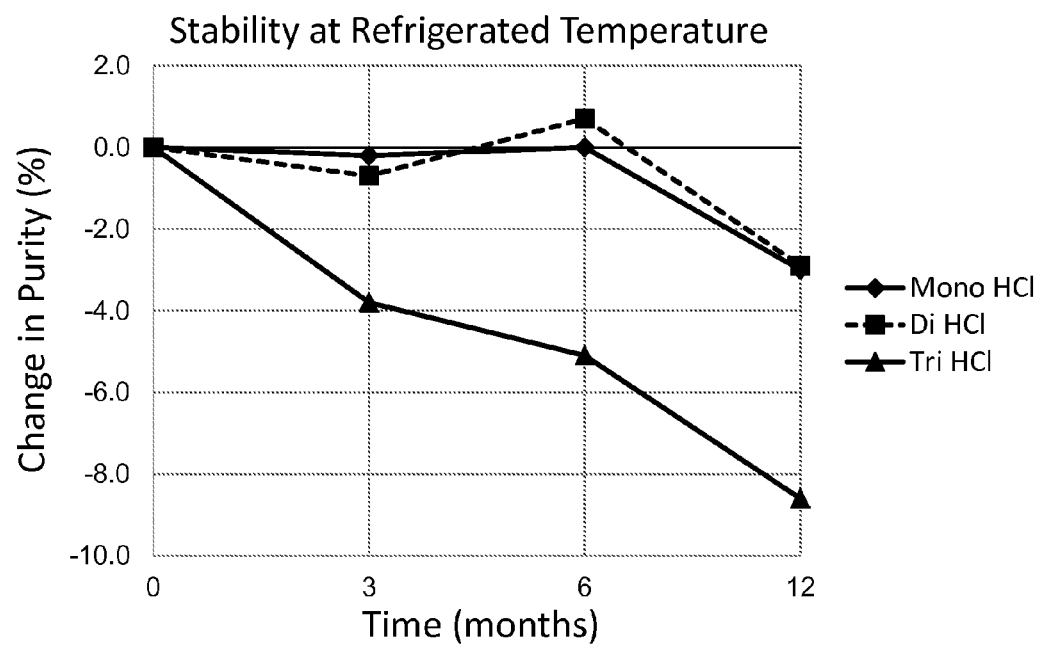
FIG. 1 shows the change in purity (percent) versus time (months) for the mono-, di- and trihydrochloride salts of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin stored at refrigerated temperature.

The present invention relates to compounds of formula I. Such compounds are acid addition salts of hydrochloric acid and 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]-carbonyl]-26-decarboxyvancomycin. In the compounds of formula I, any atom capable of being protonated by the hydrochloric acid (such as an amino group or carboxylic acid group) may be so protonated to form a salt and all such forms are included within the scope of this invention unless otherwise indicated.

Definitions

When describing this invention, the following terms have the following meanings unless otherwise indicated.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "refrigerated temperature" means a temperature of about 2° C. to about 8° C.

The term "room temperature" means ambient temperature in a chemistry laboratory, typically about 18° C. to about 25° C.

The term "therapeutically effective amount" means an amount sufficient to effect treatment when administered to a patient in need of treatment.

The term "treating" or "treatment" means:
(a) preventing a disease or medical condition from occurring, i.e., prophylactic treatment of a patient or subject;
(b) ameliorating a disease or medical condition, i.e., eliminating or causing regression of the disease or medical condition in a patient;
(c) suppressing a disease or medical condition, i.e., slowing or arresting the development of the disease or medical condition in a patient; or
(d) alleviating the symptoms of a disease or medical condition in a patient.

General Synthetic Procedures

The compounds of formula I are typically prepared by first providing or forming an aqueous composition containing 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin and from about 1 to about 2 molar equivalents of hydrochloric acid. The aqueous composition is then lyophilized to provide a compound of formula I.

The aqueous composition is typically prepared by adding the appropriate amount of dilute aqueous hydrochloric acid (such as 1 N aqueous hydrochloric acid) to an aqueous composition of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin. Generally, the aqueous composition containing the compound is analyzed by, for example, HPLC to determine the amount of the compound present in the aqueous solution. Once the amount of the compound is known, the appropriate amount of hydrochloric acid is added so that the resulting aqueous composition contains from about 1 to about 2 molar equivalents of hydrochloric acid per molar equivalent of compound. Typically, the hydrochloric acid is added at a temperature in the range of from about −10° C. to about 25° C.

In some cases, the aqueous solution may already contain some hydrochloric acid (e.g., less than 1 molar equivalent) and in such cases, the amount of hydrochloric acid already present in the aqueous solution is taken into consideration when adding additional hydrochloric acid. Alternatively, if the aqueous solution containing the 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]-amino]carbonyl]-26-decarboxyvancomycin contains more than about 2 equivalents of hydrochloric acid, the aqueous solution can be neutralized with base, such as an alkali bicarbonate, alkali carbonate and the like, to adjust the molar ratio of hydrochloric acid to the compound to be in the range of from about 1 to about 2. By way of example, sodium bicarbonate may be used as the base. The base is typically added in the form of a dilute aqueous solution, e.g., such as a 5% aqueous sodium bicarbonate solution. The base is typically added to the aqueous solution at a temperature in the range of from about −10° C. to about 25° C.

When describing such aqueous compositions, it will be recognized that the hydrochloric acid protonates the compound so that the aqueous composition contains the acid addition salt of hydrochloric acid and the compound. Thus, any reference to the molar ratio of the compound to hydrochloric acid will be understood to refer to the molar ratio of the components in the form of the acid addition salts.

Once the aqueous composition containing the compound and from about 1 to about 2 molar equivalents of hydrochloric acid has been formed, the aqueous composition is typically lyophilized to provide a compound of formula I as a lyophilized powder. The lyophilization is generally conducted at a temperature in the range of from about −60° C. to about −20° C. under reduced pressure in the range of from about 20 torr (mm Hg) to about 100 torr, such as about 40 torr to 60 torr. The lyophilization is generally conducted for about 48 hours to about 200 hours or until the volatile components are substantially removed. The lyophilization provides the compound of formula I as a lyophilized powder.

Alternatively, the compound of formula I can be precipitated and isolated by filtration or centrifugation. For example, an excess of an organic diluent can be used to precipitate the compound of formula I from an aqueous composition. Suitable organic diluents include, by way of illustration, acetonitrile, methanol, ethanol, acetone, and the like. If desired, the precipitate can optionally be washed with a suitable organic diluent. For example, when acetone is used to precipitate the compound of formula I, the resulting precipitate is optionally washed with acetone and then dried. Typically, the isolation procedure is conducted at a temperature of from about 0° C. to about 30° C., typically at a range of between about 5° C. to about 20° C., and all filtration, washing and drying steps are done under an inert atmosphere, such as nitrogen, argon and the like.

Procedures for preparing 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin are known in the art. For example, the preparation of this compound is described in U.S. Pat. No. 6,974,797 B2 and Long et al., J. Antibiot. 61(10): 603-614 (2008).

By way of illustration, vancomycin or a salt thereof can be reacted with compound A having the formula:

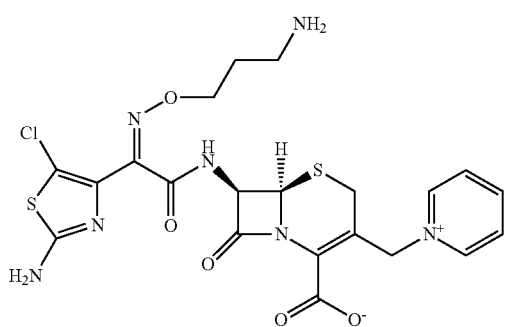

A or a salt thereof, in the presence of a peptide coupling reagent to provide 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]-carbonyl]-26-decarboxyvancomycin or a salt thereof.

Typically, this reaction is conducted by contacting vancomycin or a salt thereof, with about 1 to about 1.1 molar equivalents of a peptide coupling reagent in a diluent, such as DMF, DMSO, or a mixture thereof. This reaction is typically conducted at a temperature in the range of from about −10° C. to about 10° C. for about 10 minutes to about 60 minutes or until the reaction is substantially complete. A solution of about 0.9 to about 1.1 molar equivalents of compound A or a salt thereof in a diluent, such as DMF, DMSO or a mixture thereof, is then added to the activated vancomycin derivative. After addition of compound A, an amine, such as diisopropylethylamine, is added in an amount ranging from about 2 to about 10 molar equivalents (such as about 5 molar equivalents). The amine is typically added at rate so that the reaction temperature is maintained in the range of about −10° C. to about 5° C. The reaction mixture is then typically maintained at a temperature in the range of about −10° C. to about 5° C. for about 0.5 to about 3 hours, or until the reaction is substantially complete.

Various peptide coupling reagents can be used in this reaction. Representative examples include benzotriazol-1-yloxytripyrrolidinophosphonium hexafluorophosphate (PyBOP) with or without 1-hydroxy-7-azabenzotriazole (HOAt); O-(6-chloro-1-hydrocibenzotriazol-1-yl)-1,1,3,3-tetramethyluronium tetrafluoroborate (TCTU); O-(6-chlorobenzotriazol-1-yl)-N,N,N',N'-tetramethyluronium hexafluorophosphate (HCTU); O-(benzotriazol-1-yl)-N,N,N',N'-tetramethyluronium tetrafluoroborate (TBTU); 4-(4,6-dimethoxy-1,3,5-triazin-2-yl)-4-methylmorpholinium chloride (DMTMM); 1-ethyl-3-(3-dimethylaminopropyl)carbodiimide (EDCI) with HOAt; diethylcyanophosphonate (DECP) and the like. In one embodiment, the peptide coupling reagent is 4-(4,6-dimethoxy-1,3,5-triazin-2-yl)-4-methylmorpholinium chloride.

After the coupling reaction is complete, the reaction product is isolated and purified using conventional procedures, such as precipitation and filtration, column chromatography, HPLC and the like.

Compound A is known in the art. For example, compound A can be prepared as described in U.S. Pat. No. 6,974,797 B2 (Example A, at column 27, line 51 to column 30, line 56) or in Long et al., J. Antibiot. 61(10): 603-614 (2008) ($C_{OX}$ Synthon 18 at pages 611-612). Procedures for preparing compound A are also described in the Examples.

Vancomycin is also known in the art. For example, vancomycin hydrochloride is commercially-available from Sigma-Aldrich (St. Louis, Mo. 63103) and from Haorui Pharma-Chem Inc. (Irvine, Calif. 92618).

After preparation, the 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin employed in the present invention can be purified using reverse-phase HPLC or other chromatographic methods.

For example, the compound can be purified using poly(styrene-divinylbenzene) (PS-DVB) resins. Typically, the PS-DVB resin employed for purifying the compound is a rigid, macroporous type resin having a pore size ranging from about 100 angstroms to about 1,000 angstroms and a particle size ranging from about 10 μm to about 50 μm. A representative resin suitable for use is PLRP-S (Agilent Technologies, Santa Clara Calif. 95051) having a pore size of about 100 angstroms and a particle size of about 50 μm.

Generally, the eluent used for the purification comprises an aqueous acidic solution containing varying amounts of a polar organic solvent. Representative polar organic solvents include acetonitrile, ethanol, isopropanol, methanol, and the like. Suitable acids include acetic acid, trifluoroacetic acid, hydrochloric acid, and the like. The eluent may also contain a buffer, such as an acetate buffer or a phosphate buffer. In one embodiment, the eluent comprises an aqueous acetate buffer (100 mM) containing acetonitrile in amounts ranging from about 2% v/v to about 13% v/v.

Depending on the purification procedure employed, a salt exchange may be conducted after the purification to provide a hydrochloride salt of the compound. For example, if the acid employed in the purification procedure is an acid other than hydrochloric acid (i.e., acetic acid or trifluoroacetic acid), a salt exchange is typically conducted to form the hydrochloric acid salt.

The salt exchange is generally performed using a PS-DVB resin as described herein for the purification. The salt of the compound is typically loaded onto the PS-DVB resin and then the resin is eluted with an aqueous hydrochloric acid solution containing varying amounts of a polar organic solvent. Representative polar organic solvents include acetonitrile, ethanol, isopropanol, methanol, and the like. Generally, the amount of the polar organic solvent employed will range from about 10% v/v to about 80% v/v; including about 10% v/v to about 50% v/v; such as about 10% v/v to about 20% v/v. In one embodiment, the eluent used for the salt exchange comprises about 10 mM aqueous hydrochloric acid containing about 20% v/v acetonitrile.

Pharmaceutical Compositions

Compounds of formula I are typically administered to a patient in the form of a pharmaceutical composition. Such pharmaceutical compositions may contain any acceptable carrier or excipient. The choice of a particular carrier, or combinations of carriers, will depend on various factors, such as the mode of administration, compatibility of the components, stability of the composition, and the like.

Conventional techniques for preparing pharmaceutical compositions are known in the art and are described, for example, in REMINGTON: THE SCIENCE AND PRACTICE OF PHARMACY (REMINGTON: THE SCIENCE & PRACTICE OF PHARMACY), Pharmaceutical Press, Philadelphia, Pa.; 21$^{st}$ Ed. (Oct. 7, 2011). Additionally, conventional ingredients needed for such compositions are commercially-available from, for example, Sigma-Aldrich, St. Louis, Mo. 63178, and other commercial suppliers.

The pharmaceutical composition is typically prepared by thoroughly and intimately mixing or blending a compound of formula I with a pharmaceutically acceptable carrier and any optional ingredients.

In one embodiment, the pharmaceutical composition is suitable for parenteral administration, particularly intravenous administration. Such pharmaceutical compositions typically comprise a sterile, physiologically-acceptable aqueous carrier solution containing a compound of formula I. In one embodiment, the composition is pyrogen-free. Optionally, the carrier solution may contain other components, such as sugars, amino acids, electrolytes and the like.

Representative physiologically-acceptable aqueous carriers include, by way of example, Sterile Water for Injection, USP; Dextrose Injection, USP (e.g., 2.5, 5.0, 10, 20% dextrose, including 5% Dextrose Injection (D5/W)); Dextrose and Sodium Chloride Injection, USP (e.g., dextrose varying from 2.5 to 10% and sodium chloride varying from 0.12 (19 mEq sodium) to 0.9% (154 mEq sodium)); Mannitol Injection, USP, (e.g., 5, 10, 15, 20 and 25% mannitol); Ringer's Injection, USP (e.g., 147 mEq sodium, 4 mEq potassium, 4.5 mEq calcium and 156 mEq chloride per liter); Lactated Ringer's Injection, USP (e.g., 2.7 mEq calcium, 4 mEq potassium, 130 mEq sodium, and 28 mEq lactate per liter); Sodium Chloride Injection, USP (e.g., 0.9% sodium chloride) and the like.

When administered to a patient, the compound of formula I will typically be diluted in about 0.5 mL to about 10 mL of the aqueous carrier per mg of the compound of formula I, such as about 0.6 to about 8 mL per mg.

Alternatively, the pharmaceutical composition may be in a solid form suitable for reconstitution and subsequent parenteral administration. Such compositions are typically in the form a sterile, lyophilized composition which is reconstituted prior to use with a sterile, physiologically-acceptable aqueous carrier. In this embodiment, the pharmaceutical composition typically comprises a compound of formula I and a pharmaceutically-acceptable carrier. Representative carriers for use in such pharmaceutical compositions include, by way of example, sucrose, mannitol, dextrose, dextran, lactose, glycine or combinations thereof.

In one embodiment, the pharmaceutical composition comprises (a) a compound of formula I, (b) sucrose and (c) glycine or a pharmaceutically-acceptable salt thereof. Such compositions typically contain about 0.5 to about 2.0 parts by weight, including about 1.0 part by weight, of sucrose per part by weight of the compound of formula I (as the free base equivalent); and about 0.5 to about 2.0 parts per weight, including about 1.5 parts per weight, of glycine (as the free base equivalent) per part by weight of the compound of formula I (as the free base equivalent). In one embodiment, the pharmaceutical composition contains about 1.0 part by weight sucrose and about 1.5 parts per weight of glycine (as the free base equivalent) per part by weight of the compound of formula I (as the free base equivalent). For example, such pharmaceutical compositions may comprise from about 0.5 mg to about 2.0 mg of sucrose and about 1.0 mg to about 2.0 mg of glycine (as the free base equivalent) per milligram of compound of formula I (as the free base equivalent), such as about 1.0 mg of sucrose and about 1.5 mg of glycine (as the free base equivalent) per milligram of compound of formula I (as the free base equivalent).

In another embodiment, the pharmaceutical composition comprises (a) about 10 wt. % to about 60 wt. % of the compound of formula I (free base equivalent); (b) about 10 wt. % to about 60 wt. % of sucrose; and (c) about 10 wt. % to about 80 wt. % of glycine (free base equivalent). For example, this embodiment includes a pharmaceutical composition comprising (a) about 20 wt. % to 50 wt. % of the compound of formula I (free base equivalent); (b) about 20 wt. % to 50 wt. % of sucrose; and (c) about 20 wt. % to about 70 wt. % of glycine (free base equivalent); such as a pharmaceutical composition comprising (a) about 25 wt. % to 35 wt. % of the compound of formula I (free base equivalent); (b) about 25 wt. % to 35 wt. % of sucrose; and (c) about 30 wt. % to about 50 wt. % of glycine (free base equivalent); based on the total weight of the composition.

In one embodiment, the pharmaceutical composition is a lyophilized powder. Typically, the lyophilized powder is sterile and is packaged in a hermetically-sealed vial or ampoule or similar container.

Storage Stability

Compounds of formula I have been discovered to have significantly improved storage stability compared to the corresponding trihydrochloride salt. Additionally, the storage stability of compounds of formula I has been found to be further improved in compositions containing sucrose and glycine.

Figure 2:
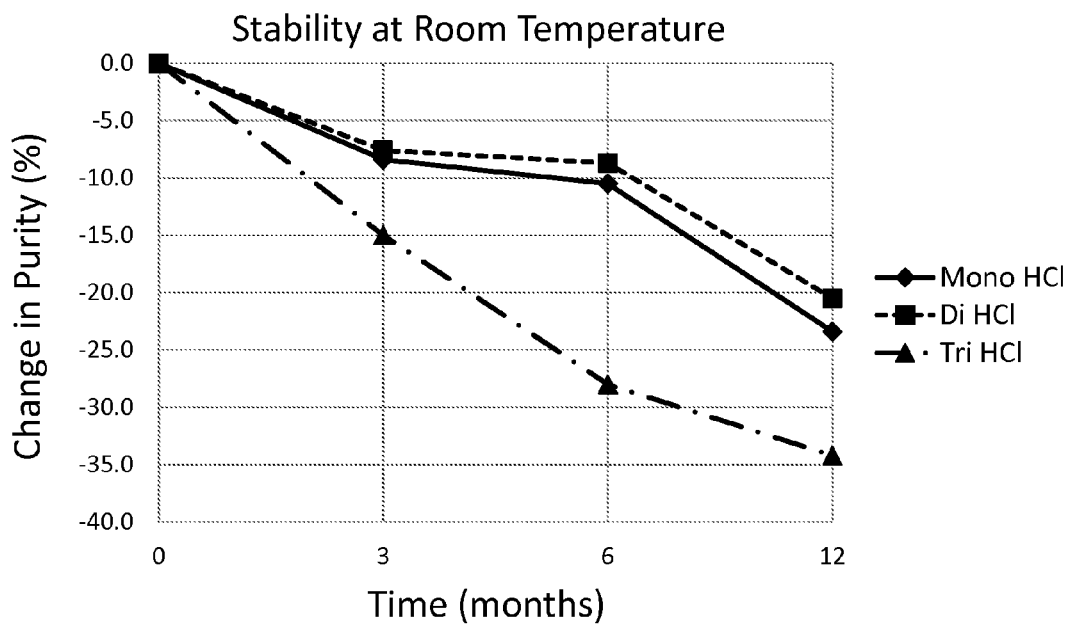
FIG. 2 shows the change in purity (percent) versus time (months) for the mono-, di- and trihydrochloride salts of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin stored at room temperature.

The trihydrochloride salt of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin is known in the art. For example, the trihydrochloride salt is described in U.S. Pat. No. 6,974,797 B2 at column 35, lines 16-20. However, upon storage, the purity of the trihydrochloride salt has been found to decrease significantly. For example, when stored at room temperature for 12 months, the trihydrochloride salt has been found to decrease in purity by over 30% (as shown in FIG. 2).

Such degradation is of concern because the degradation products may differ in their biological activity or therapeutic effect compared to the parent molecule. See, for example, J. Diana et al., *Journal of Chromatography A*, 996:115-131 (2003), which discusses vancomycin impurities.

One of the degradation products of the trihydrochloride salt is believed to be a compound of formula II:

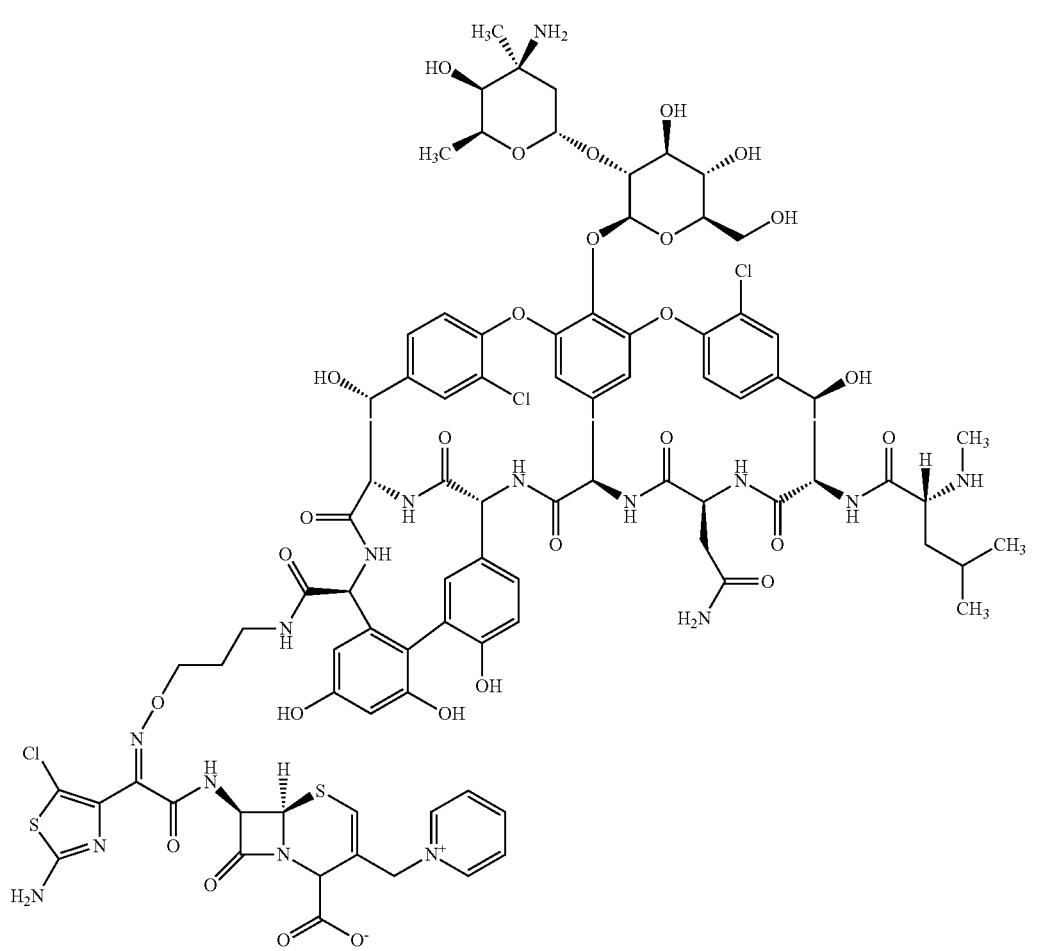

or a salt thereof. This compound is also referred to as Degradant B. The compound of formula II is a double-bond isomer in which the double bond in the A-ring of the cephalosporin moiety has isomerized from the $\Delta^3$ position to the $\Delta^2$ position. $\Delta^2$ isomers of cephalosporin acids have been reported to be inactive. See, for example, Crocker et al, *J. Chem. Soc. (C)*, 1142 (1966); and Saab et al., *J. Pharm. Sci.*, 77(10), 906 (1988). Therefore, it is important to minimize the formation of the $\Delta^2$ isomer during storage of the compound.

Another degradant is believed to be a hydrolysis product having formula III:

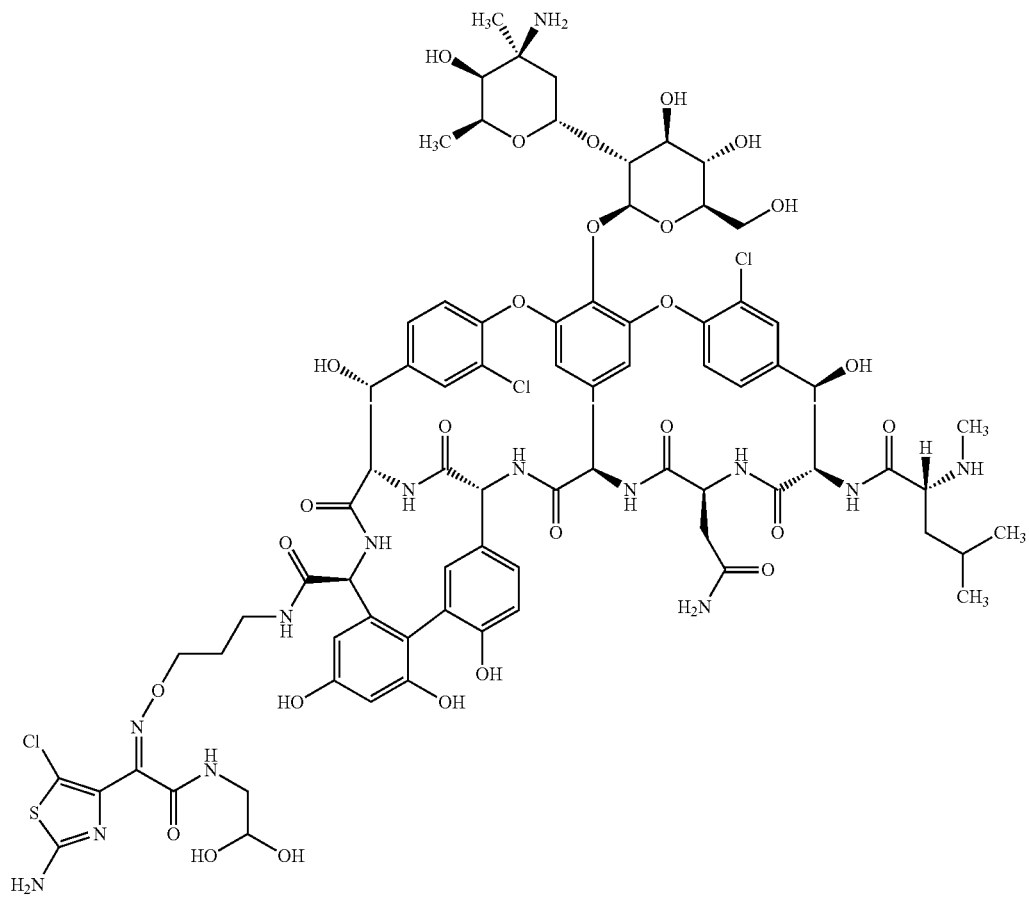

or a salt thereof. The compound of formula III is also referred to as Degradant A.

It has now been discovered that compounds of formula I are more stable compared to the trihydrochloride salt when stored at room temperature or refrigerated temperature for 12 months. See, for example, FIGS. 1 and 2.

Additionally, compounds of formula I are more stable at room temperature when they are formulated with sucrose and glycine. See, for example, FIGS. 3, 4 and 5.

In one embodiment, the change (or decrease) in purity of the compound of formula I in the pharmaceutical composition is less than about 10% as measured by high performance liquid chromatography ("HPLC") after storage for 12 months at a temperature in the range of from about 18° C. to about 25° C. (room temperature).

In another embodiment, the area-under-the-curve (AUC) for the compound of formula I decreases by less than about 10% as determined by high performance liquid chromatography ("HPLC") after storage of the pharmaceutical composition for 12 months at a temperature in the range of from about 18° C. to about 25° C. (room temperature).

In a particular embodiment, the invention provides a pharmaceutical composition comprising:
(a) a compound of formula I;
(b) about 1.0 parts by weight of sucrose; and
(c) about 1.5 parts by weight of glycine (as the free base equivalent);

wherein the parts by weight of sucrose and glycine are based on the part by weight of the compound of formula I (as the free base equivalent); and wherein change in purity of the compound of formula I in the pharmaceutical composition is less than about 10% as measured by high performance liquid chromatography after storage for 12 months at a temperature in the range of from about 18° C. to about 25° C.

Utility

26-[[[3-[[(Z)-[1-(2-Amino-5-chloro-4-thiazolyl)-2-[[(6R, 7R)-2-carboxy-8-oxo-3-(pyridiniomethyl)-5-thia-1-azabicyclo[4.2.0]oct-2-en-7-yl]amino]-2-oxoethylidene]-amino]oxy]propyl]amino]carbonyl]-26-decarboxyvancomycin and salts thereof have utility as antibiotics or bactericidal agents against Gram-positive bacteria, including multidrug-resistant organisms such as methicillin-resistant *Staphylococcus aureus* (MRSA) and vancomycin-intermediate *S. aureus* (VISA). See, for example, Leuthner et al., *Antimicrob. Agents Chemother.* 2010, 54(9):3799; Hegde et al., *Antimicrob. Agents Chemother.* 2012, 56(3):1578; Blais et al., *Antimicrob. Agents Chemother.* 2012, 56(3):1584; and Tyrell et al., *Antimicrob. Agents Chemother.* 2012, 56(4):2194.

The minimum inhibitory concentration (MIC) of compounds of formula I against various bacteria and bacterial strains can be determined using standard procedures, such as those published by the Clinical and Laboratories Standards Institute (CLSI) (Wayne, Pa. 19087). See, for example, CLSI. *Methods for Dilution Antimicrobial Susceptibility Tests for Bacteria That Grow Aerobically; Approved Standard—Ninth*

Compounds of formula I are typically administered in a therapeutically effective amount by any acceptable route of administration. Typically, the compounds are administered parenterally, such as intravenously. The compounds may be administered in a single daily dose or in multiple doses per day. The treatment regimen may require administration over extended periods of time, for example, for several days or for one to six weeks or longer. The amount of compound administered per dose or the total amount administered will typically be determined by the patient's physician and will depend on such factors as the nature and severity of the infection, the age and general health of the patient, the tolerance of the patient to the compound, the microorganism(s) causing the infection, the route of administration and the like.

Representative doses range from about 0.25 to about 2.5 mg/kg/day of the compound of formula I (free base equivalent), including from about 1 to about 2 mg/kg/day. In one embodiment, the compound of formula I is administered at a dose of about 2 mg/kg/day (free base equivalent). A representative treatment regimen consists of administering a compound of formula I once per day at a dose of about 2 mg/kg/day (free base equivalent) for a period of about 7 to about 14 days.

When administered in a physiologically-acceptable aqueous carrier, the compound of formula I is typically administered intravenously to the patient over a period of about 0.5 h to about 2 h, such as for about 1 h.

Representative infections or bacteria-related medical conditions that can be treated or prevented with a compound of formula I include, by way of example, infections caused by Gram-positive bacteria, including skin and skin structure infections, pneumonia, endocarditis, meningitis, sepsis, urinary tract infections, blood stream infections, osteomyelitis, and the like. When treating such conditions, the patient may already be infected with the microorganism to be treated or may be susceptible to infection in which case the antibiotic agent is administered prophylactically.

EXAMPLES

The following examples are provided to illustrate various representative embodiments and aspects of this invention and are not intended to limit the scope of this invention in any way unless specifically indicated.

Vancomycin hydrochloride was purchased from Haorui Pharma-Chem Inc., Irvine, Calif., USA. 4-(4,6-Dimethoxy-1,3,5-triazin-2-yl)-4-methylmorpholinium chloride (DMTMM) was purchased from Ubichem Plc, Hampshire, UK. 1-[[(6R,7R)-7-Amino-2-carboxy-8-oxo-5-thia-1-azabicyclo[4.2.0]oct-2-en-3-yl]methyl]pyridinium chloride monohydrochloride (7-PYCA) was purchased from Zhejiang Hengdian Apeloa Imp. & Exp. Co., Ltd., Zhejiang, China, and Aurisco Pharmaceuticals Limited, Shanghai, China; or it can be prepared by the procedure in, e.g., U.S. Pat. No. 4,258,041, or by other published procedures. All other reagents, starting materials and solvents used in the following examples were purchased from commercial suppliers (such as Sigma-Aldrich Chemical Company, St. Louis, Mo.) and were used without further purification unless otherwise indicated.

The following abbreviations are used: DMF=N,N-dimethylformamide; DMSO=dimethyl sulfoxide; h=hours; and min=minutes.

Example 1

HPLC Method for Determining the Purity of 26-[[[3-[[(Z)-[1-(2-Amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]-propyl]amino]carbonyl]-26-decarboxyvancomycin Samples Test samples were assayed for 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]-oct-2-en-7-yl] amino]-2-oxoethylidene]amino]oxy]propyl]amino] carbonyl]-26-decarboxyvancomycin and its degradation products using an HPLC system with a photodiode array detector (Agilent 1100 or 1200 HPLC System; Agilent Technologies Inc., Santa Clara, Calif. 95051) controlled with chromatography data software (Empower Software, Waters Corporation, Milford, Mass. 01757). All solvents were HPLC grade and were purchased from Honeywell Burdick & Jackson (Muskegon, Mich. 49442). Phosphoric acid (85% w/w) and sodium dihydrogen phosphate were HPLC grade and were purchased from Fluka (Sigma-Aldrich, St. Louis, Mo. 63103). All reagents were used without further purification.

Test samples were filtered through a 0.2 μm polyvinylidene fluoride (PVDF) filter before analysis and the first 1 mL was discarded. The HPLC analysis conditions are summarized in Table A.

TABLE A

HPLC Analysis Conditions

| | | | |
|---|---|---|---|
| Column | Advanced Materials Technology Halo C18 Column, 2.7 μm, 4.6 × 150 mm | | |
| Autosampler Temp. | 5.0° C. | | |
| Column Temp. | 30.0° C. | | |
| Wavelength | 214 nm | | |
| Mobile Phase A | 2:98 acetonitrile:water w/ 65 mM phosphate buffer pH = 2.0 | | |
| Mobile Phase B | 60:40 acetonitrile:water w/ 65 mM phosphate buffer pH = 2.0 | | |
| Sample Solvent | 2:98 acetonitrile:water w/ 65 mM phosphate buffer pH = 3.2 | | |
| Sample Conc. | 0.25 mg/mL | | |
| Injection Volume | 7 μL | | |
| Flow Rate | 1.00 mL/min | | |
| | Time (min) | Mobile Phase A | Mobile Phase B |
| Gradient | 0 | 92.0% v/v | 8.0% v/v |
| | 93.0 | 70.0 | 30.0 |
| | 98.0 | 45.0 | 55.0 |
| | 98.1 | 5.0 | 95.0 |
| | 100.1 | 5.0 | 95.0 |
| | 100.2 | 92.0 | 8.0 |
| | 105.0 | 92.0 | 8.0 |

The retention times for particular sample components are shown in Table B.

TABLE B

HPLC Retentions Times

| Compound | Retention Time (min) |
|---|---|
| Degradant A | 23.4 |
| Degradant B | 24.5 |

TABLE B-continued

HPLC Retentions Times

| Compound | Retention Time (min) |
|---|---|
| 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]-oct-2-en-7-yl]amino]-2-oxoethylidene]amino]oxy]propyl]amino]carbonyl]-26-decarboxyvancomycin | 27.2 |

Test sample purity was determined based on the integrated peak area (area-under-the-curve or AUC) for the compound as a percentage of all integrated peaks. The concentration (assay value) of the compound in a test sample was determined by comparison with a reference standard.

Example 2

GC Method for Determining Residual Solvent

Residual solvents in test samples of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]-oct-2-en-7-yl]amino]-2-oxoethylidene]amino]oxy]propyl]amino]carbonyl]-26-decarboxyvancomycin were determined using a gas chromatography system (Agilent GC 6890, Agilent Technologies, Santa Clara Calif. 9505) equipped with a head-space autosampler (Agilent 7694 Headspace Sampler). A DB-624 GC column (30 m length×0.53 mm ID×3 µm) was used (Agilent, Part No. 125-1334).

An internal standard solution was prepared by adding 1-butanol (4 mL) to a 1 L volumetric flask. DMSO (800 mL) was added and the mixture was mixed thoroughly and then additional DMSO was added to make a total volume of 1 L.

Each test sample (50 mg) was transferred to a 20 mL headspace vial and the internal standard solution (1 mL) was added and the resulting mixture was agitated vigorously until the sample was dissolved.

Reference standards were prepared having a concentration of 2 mg/mL in the internal standard solution from commercially available solvents of known purity. All reference standard solvents were typically combined into one reference standard solution which was prepared in triplicate. For each reference standard replicate, 1 mL of the solution was added to the 20 mL headspace vial and crimp sealed.

The GC analysis conditions are summarized in Table C.

TABLE C

GC Analysis Conditions

| Carrier Gas | Helium at 2.60 mL/min constant flow | | |
|---|---|---|---|
| GC Oven | Equilibration Time = 1 min | | |
| | Total Run Time = 29.7 min | | |
| GC Oven Ramp | Ramp Rate (° C./min) | Final Temp. (° C.) | Run Time (min) |
| Initial | — | 30 | 0 |
| Ramp 1 | 2 | 60 | 15 |
| Ramp 2 | 10 | 140 | 23 |
| Ramp 3 | 1 | 143 | 26 |
| Ramp 4 | 10 | 160 | 29.7 |
| Inlet | 200° C.; 10:1 split ratio | | |
| Headspace Sampler | Headspace Oven = 85° C. | | |
| | Loop Temperature = 100° C. | | |
| | Transfer Line = 110° C. | | |
| | Vial Equilibrium Time = 10 min, on high shake | | |
| | Vial Pressurization = 11 psi (He) | | |
| | 1 mL Sample Loop | | |

TABLE C-continued

GC Analysis Conditions

| Detector | FID, 300° C. |
|---|---|
| | Hydrogen Flow = 30 mL/min |
| | Air Flow = 400 mL/min |
| | Nitrogen makeup gas at 30 mL/min |

GC retention times for typical solvents relative to the 1-butanol internal standard are shown in Table D. 1-Butanol typically elutes at about 19.0 min.

TABLE D

Relative GC Retentions Times Compared to 1-Butanol

| Solvent | Relative Retention Time |
|---|---|
| Acetone | 0.45 |
| Acetonitrile | 0.50 |
| 1-Butanol | 1.00 |
| Dimethyl sulfoxide | 1.38 |
| Methyl tert-butyl ether | 0.57 |

The amount of residual solvent in a test sample was determined by comparing the peak areas of the sample to those of the reference standards.

Example 3

Preparation of tert-Butyl 3-Bromopropylcarbamate

To a solution of sodium hydroxide (105 g, 2.625 mol) in water (1.15 L) maintained at a temperature at or slightly below 10° C. was added a solution of di-tert-butyl dicarbonate (229 g, 1.05 mol) in heptane (1.03 L). The flask containing the solution of di-tert-butyl dicarbonate was rinsed with heptane (125 mL) and the rinsate was added to the reaction mixture. The resulting mixture was cooled to a temperature at or slightly below 10° C. and a solution of 3-bromopropylamine hydrobromide (251 g, 1.15 mol) in water (250 mL) was added dropwise at a rate that allowed the internal reaction temperature to be maintained below about 20° C. The flask containing the solution of 3-bromopropylamine hydrobromide was rinsed with water (20 mL) and the rinsate was added to the reaction mixture. After the addition was complete, the reaction mixture was allowed to slowly warm to room temperature (about 22° C.) and stirring was continued for about 2 h at room temperature. The stirring was discontinued and the mixture was allowed to stand for 30 min. The lower aqueous layer was separated from the organic layer and discarded. To the organic layer was added a saturated aqueous sodium chloride solution (250 mL) and the resulting mixture was stirred for 5 min. The mixture was allowed to stand for 30 min and the lower aqueous layer was separated and discarded. The organic layer was concentrated to a volume of about 350 mL and this concentrated solution was cooled to 5° C. and stirred for 4 h at 5° C. The resulting precipitate was collected by vacuum filtration to provide the title compound as a white crystalline solid (211 g, 84% yield). The filtrate was concentrated and the concentrated solution was cooled to 5° C. and stirred for 4 h at 5° C. The resulting additional precipitate was collected by vacuum filtration to provide an additional amount of the title compound (17 g, 6.8% yield). $^1$H NMR (400 MHz, DMSO-$d_6$) δ $^1$H NMR (400 MHz, DMSO-$d_6$) δ 3.50 (t, J=6.8 Hz, 2H), 3.03 (q, J=6.8 Hz, 2H), 1.91 (m, J=6.8 Hz, 2H), 1.38 (s, 9H).

Example 4

Preparation of Ethyl (2Z)-2-(2-Aminothiazol-4-yl)-2-(3-N-tert-butoxycarbonylaminopropoxyimino)acetate To a mixture of ethyl 2-amino-α-(hydroxyimino)-4-thiazoleacetate (139.9 g, 650 mmol), tert-butyl 3-bromopropylcarbamate (209.0 g, 877.5 mmol) and powdered potassium carbonate (157.2 g, 1137.5 mmol) was added DMF (550 mL) and water (24.4 mL). The resulting mixture was stirred at 30° C. for about 11 h. The reaction mixture was cooled to room temperature and ethyl acetate (2.3 L) and water (1.7 L) were added and the resulting mixture was stirred for 5 min. The mixture was allowed to stand for 60 min and the lower layer (aqueous layer) was separated and discarded. An aqueous sodium bicarbonate solution (10 wt. %, 600 mL) was added and the resulting mixture was stirred for 5 min. The mixture was allowed to stand for 60 min and the lower layer (aqueous layer) was separated and discarded. An aqueous sodium chloride solution (10 wt. %, 600 mL) was added and the resulting mixture was stirred for 5 min. The mixture was allowed to stand for 60 min and the lower layer (aqueous layer) was separated and discarded. The organic layer was concentrated to a volume of about 600 mL. Hexanes (250 mL) were added dropwise to the concentrate with gently stirring at 0° C. for 1 h to form a precipitate. The precipitate was collected by vacuum filtration to give the title compound (232 g, 96% yield) as an off-white crystalline solid. $^1$H NMR (400 MHz, DMSO-$d_6$) δ 7.25 (s, 2H), 6.89 (s, 1H), 6.82 (brs, 1H), 4.26 (q, J=8 Hz, 2H), 4.08 (t, J=6.4 Hz, 2H), 2.97 (q, J=6.4 Hz, 2H), 1.72 (m, J=6.4 Hz, 2H), 1.37 (s, 9H), 1.26 (t, J=8 Hz, 3H).

If desired, the product can be recrystallized. The crude material from several batches (1.0 kg, 91.2% purity) was dissolved in ethyl acetate (2 L) at 60° C. and heptane (1 L) was added slowly. The resulting solution was heated to 60° C. for 1 h with stirring during which time a precipitate formed. The mixture was then allowed to cool slowly to room temperature. The precipitate was collected by vacuum filtration under dry nitrogen, washed with a mixture of heptane and EtOAc (1 L, 3:1) and dried under vacuum overnight to give the title compound (770 g, 98.3% purity).

Example 5

Preparation of (2Z)-2-(2-Aminothiazol-4-yl)-2-(3-N-tert-butoxycarbonylaminopropoxyimino)acetic Acid To a solution of ethyl (2Z)-2-(2-aminothiazol-4-yl)-2-(3-N-tert-butoxycarbonylaminopropoxyimino)acetate (232.0 g, 622.9 mmol) in absolute ethanol (1.63 L) was added dropwise a solution of sodium hydroxide (29.9 g, 747.4 mmol) in water (748 mL). The resulting mixture was heated at 35° C. for about 8 h. The mixture was then cooled to about −5° C. and trifluoroacetic acid (about 10 mL) was added dropwise until the pH of the mixture was about 6.0. The mixture was then concentrated under vacuum to remove most of the volatile components and absolute ethanol (500 mL) was added. The resulting mixture was concentrated again to remove water via an azeotrope. This procedure was repeated again by adding absolute ethanol (500 mL) followed by concentrating to give the title compound which was used in the next reaction without any further isolation or purification.

Example 6

Preparation of (2Z)-2-(2-Amino-5-chlorothiazol-4-yl)-2-(3-N-tert-butoxycarbonylaminopropoxyimino)acetic Acid Triethylamine Salt Ethyl acetate (2.0 L) was added to a mixture of (2Z)-2-(2-aminothiazol-4-yl)-2-(3-N-tert-butoxycarbonylaminopropoxyimino)acetic acid (about 213 g, 627 mmol) in methanol (200 mL) to form a slurry. N-Chlorosuccinimide (108.0 g, 815 mmol) was added and the resulting mixture was stirred at room temperature for 3 h. Water (2.5 L), sodium chloride (514 g) and trifluoroacetic acid (93 mL, 1254 mmol) were added and the resulting mixture was stirred for 15 min. The mixture was allowed to stand for 1 h and then the lower aqueous layer was separated and discarded. The organic layer was concentrated under vacuum to a volume of about 500 mL. Acetonitrile (1.0 L) was added and the mixture was concentrated under vacuum. This was repeated by again adding acetonitrile (1.0 L) and concentrating the mixture under vacuum to a volume of about 600 mL. The mixture was then filtered through diatomaceous earth (Celite). Triethylamine (350 mL, 2508 mmol) was added and the mixture was cooled to 0° C. at which time a precipitate formed. The precipitate was collected by vacuum filtration, rinsed with acetonitrile (165 mL), and dried at room temperature under vacuum to give the title compound (224 g, 79% yield) as a light brown crystalline solid. $^1$H NMR (400 MHz, MeOH-$d_4$) δ 4.15 (t, J=6.4 Hz, 2H), 3.18 (m, 8H), 1.86 (m, 2H), 1.43 (s, 9H), 1.30 (t, J=7.9 Hz, 9H).

Example 7

Preparation of 1-[[(6R,7R)-7-[[(2Z)-(2-Amino-5-chloro-4-thiazolyl)][(3-N-tert-butoxycarbonylaminopropoxy)imino]acetyl]amino]-2-carboxy-8-oxo-5-thia-1-azabicyclo[4.2.0]oct-2-en-3-1]methyl]pyridinium Hydrochloride To a mixture of (2Z)-2-(2-amino-5-chlorothiazol-4-yl)-2-(3-N-tert-butoxycarbonylaminopropoxyimino)acetic acid triethylamine salt (44.88 g, 93.5 mmol) in dimethylacetamide (300 mL) at 20° C. was added dithiobis(benzothiazole) (32.7 g, 98.2 mmol). Triphenylphosphine (25.8 g, 98.2 mmol) was added (slight exotherm) and the resulting mixture was stirred for 30 min at room temperature during which time the reaction mixture became a red-brown clear solution. The reaction mixture was cooled to 0° C. and diisopropylethylamine (14.8 mL, 85 mmol) was added. The resulting mixture was stirred for about 5 min and then 1-[[(6R,7R)-7-amino-2-carboxy-8-oxo-5-thia-1-azabicyclo[4.2.0]oct-2-en-3-yl]methyl]pyridinium chloride monohydrochloride (7-PYCA) (34.00 g, 85.0 mmol) was added. The resulting mixture was stirred at 0° C. for 16 h and then a solution of hydrochloric acid in 1,4-dioxane (4.0 M, 44.6 mL, 178.5 mmol) was added slowly while maintaining the internal temperature of the reaction mixture between about 0° C. to about 5° C. The resulting mixture was stirred for about 20 min and then filtered through filter paper. The filtrate was then added slowly over a 30 min period to ethyl acetate (2.5 L) at room temperature to form a precipitate. The resulting slurry was stirred for about 1 h at room temperature and then the precipitate was collected by filtration under a dry nitrogen atmosphere. The wet cake was washed with ethyl acetate (1×300 mL) and methyl tert-butyl ether (1×300 mL), then dried under a stream of dry nitrogen for about 25 min. The material was then dried in a vacuum oven for 4 h at room temperature to provide the title compound (56.6 g, about 85% purity).

Example 8

Preparation of 1-[[(6R,7R)-7-[[(2Z)-(2-Amino-5-chloro-4-thiazolyl)][(3-aminopropoxy)imino]acetyl]amino]-2-carboxy-8-oxo-5-thia-1-azabicyclo[4.2.0]oct-2-en-3-1]methyl]pyridinium Dihydrochloride To methanol (187.5 mL, 4751.9 mmol) at −10° C. was added acetyl chloride (138.8 mL, 1952.1 mmol) dropwise at rate sufficient to maintain the internal temperature at or below 15° C. Following the addition, the reaction mixture was warmed to room temperature and stirred for 1 h. The reaction mixture was then added dropwise to a mixture of 1-[[(6R, 7R)-7-[[(2Z)-(2-amino-5-chloro-4-thiazolyl)][(3-N-tert-butoxycarbonylaminopropoxy)imino]acetyl]amino]-2-carboxy-8-oxo-5-thia-1-azabicyclo[4.2.0]oct-2-en-3-1]methyl]pyridinium hydrochloride (50.0 g, 65.1 mmol) in methanol (187.5 mL) cooled to −10° C. The addition was conducted a rate sufficient to maintain the internal temperature of the reaction mixture at or below 0° C. The resulting mixture was stirred at 0° C. for about 6 h and then it was added dropwise to acetone (1.50 L). The resulting mixture was stirred at room temperature for 1 h and then the precipitate was collected by filtration under a dry nitrogen atmosphere. The wet cake was washed with a 1:1 v/v mixture of isopropyl alcohol and isopropyl acetate (1×600 mL) and then with methyl tert-butyl ether (1×600 mL). The material was then dried in a vacuum oven (with a nitrogen bleed) at room temperature for about 4 h to provide the title compound (33.34 g, about 93.1% purity). A second crop of the title compound was also isolated from the filtrate in a similar manner (2.6 g, about 90.6% purity).

Example 9

Preparation of 26-[[[3-[[(Z)-[1-(2-Amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin Trihydrochloride To a stirred solution of vancomycin hydrochloride (56.56 g, 38.07 mmol) in a mixture of DMSO (280.0 mL) and DMF (218.4 mL) at 0° C. was added a slurry of 4-(4,6-dimethoxy-1,3,5-triazin-2-yl)-4-methylmorpholinium chloride (12.04 g, 43.51 mmol) in DMSO (30.80 mL) and DMF (30.80 mL). The resulting mixture was stirred at 0° C. for about 20 minutes and then a mixture of 1-[[(6R,7R)-7-[[(2Z)-(2-amino-5-chloro-4-thiazolyl)][(3-aminopropoxy)imino]acetyl]amino]-2-carboxy-8-oxo-5-thia-1-azabicyclo[4.2.0]oct-2-en-3-1]methyl]pyridinium dihydrochloride (28.00 g, 31.4 mmol) in DMSO (30.80 mL) and DMF (92.40 mL) was added. The resulting mixture was cooled to −10° C. and stirred for 10 minutes. To this mixture was added N,N-diisopropylethylamine (DIPEA)(27.58 mL, 158.34 mmol) at rate that allowed the reaction temperature to be maintained below −5° C. Following complete addition of the DIPEA, the reaction mixture was stirred at −10° C. to about 1 hour (at which time, HPLC analysis showed the reaction to be substantially complete). To the reaction mixture was added 1 N aqueous hydrochloric acid (186.76 mL) at a rate that allowed the reaction temperature to be maintained below 0° C. Following complete addition of the hydrochloric acid, the reaction mixture was warmed to 10° C. and a mixture of acetonitrile (560.0 mL) and water (92.40 mL) was added. Acetone (1.40 L) was then added to the reaction mixture over a period of about 1 hour and the resulting slurry was stirred for about 30 minutes. The slurry was then filtered under nitrogen to collect the solid (wet cake). The wet cake was washed with acetone (621.60 mL) and purged with nitrogen until dry. Acetone (621.60 mL) was added to the wet cake and the resulting mixture was stirred to form a slurry and then filtered under nitrogen to collect the solid which was purged with nitrogen for about 20 minutes. The solid was then dried under vacuum at room temperature for about 18 h to provide the title compound as the trihydrochloride salt (81.9 g, 39.12 mmol, 92.2% yield).

Example 10

Purification of 26-[[[3-[[(Z)-[1-(2-Amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin A 150 mL laboratory glass column was packed with poly(styrene-divinylbenzene) copolymer (PLRP-S, 100 Å, 50 µM) and equilibrated with 98:2 v/v acetate buffer (100 mM)/acetonitrile solution for about 40 minutes at a flow rate of 15 mL/min. A solution of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin trihydrocholride (9.0 g, 4.30 mmol) in 98:2 v/v acetate buffer/acetonitrile solution (120 mL) was then loaded onto the equilibrated column. The column was eluted with 98:2 v/v acetate buffer/acetonitrile solution for about 10 minutes at a flow rate of 15 mL/min and then with 93:7 v/v acetate buffer/acetonitrile solution for about 62 minutes at a flow rate of 15 mL/min (at which time impurities had stopped eluting). The column was then eluted successively with (i) 92:8 v/v acetate buffer/acetonitrile solution for about 80 minutes; (ii) 91:9 v/v acetate buffer/acetonitrile solution for about 15 minutes; (iii) 89:11 v/v acetate buffer/acetonitrile solution for about 20 minutes; and (iv) 87:13 v/v acetate buffer/acetonitrile solution for 20 to 30 minutes (all at a flow rate of 15 mL/min) During the elution, the eluent was monitored using a UV detector at 254 nM and fractions containing the title compound were collected. Fractions containing the title compound were combined to give a solution of the title compound as the tri-acetate salt in about 1,500 mL of acetate buffer/acetonitrile solution.

Example 11

Salt Exchange to Form 26-[[[3-[[(Z)-[1-(2-Amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin Dihydrochloride A 150 mL laboratory glass column was packed with poly(styrene-divinylbenzene) copolymer (PLRP-S, 100 Å, 50 µM) and equilibrated with 98:2 v/v acetate buffer (100 mM)/acetonitrile solution for about 2.25 h at a flow rate of 15 mL/min. The solution of the title compound as the tri-acetate salt in acetate buffer/acetonitrile solution (about 1500 mL) was diluted with water (4.6 L) and the resulting solution was loaded onto the column at a flow rate of 15-30 mL/min over a period of 4.65 h. The column was eluted with 98:2 v/v 20 mM aqueous hydrochloric acid/acetonitrile solution (600 mL) at a flow rate of 10-15 mL/min (about 48 min). The column was then eluted with 80:20 v/v 10 mM aqueous hydrochloric acid/acetonitrile solution at a flow rate of 15 mL/min for 25 min. During the elution, the eluent was monitored using a UV detector at 254 nM and the eluent containing the title compound was collected. The pH of the solution containing the title compound was 2.2 (at 13° C.). The pH of the solution was adjusted to 4.27 (at 14° C.) by adding 5 wt. % aqueous sodium bicarbonate solution. The resulting solution, containing primarily the dihydrochloride salt of the title compound, had a total volume of 212 mL. This solution was determined to contain 26.0 mg/mL of the title compound (as free base equivalent) by HPLC. The solution was diluted with cold water (212 mL) to give a solution having a total volume of 424 mL and containing 13 mg/mL of the title compound (as free base equivalent).

Example 12

Preparation of Stability Samples

A. Monohydrochloride Salt (Formula I, where x is about 1)

The pH of a salt exchange solution of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]-carbonyl]-26-decarboxyvancomycin dihydrocholoride (124 mL, 13.0 mg/mL free base) was adjusted to pH 6.5 by adding 5 wt. % aqueous sodium bicarbonate solution.

Samples (2 mL each) of this solution were placed in 21 vials with vented rubber stoppers. The vials were lyophilized at −40° C. under vacuum (40-60 mTorr) for about 5 days to give 21 vials containing monohydrochloride salt (26 mg as free base equivalent) (formula I where x is about 1) as a lyophilized powder.

Analysis of representative vials showed the samples had a water content of 1.7% (Karl Fisher), residual solvent (acetonitrile) of 0.6% (GC analysis) and a purity of 90.4% (HPLC analysis).

B. Monohydrochloride Salt (Formula I, x is about 1), Sucrose and Glycine

To a solution of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin monohydrochloride (75 mL, 13.0 mg/mL, 975 mg) was added sucrose (975 mg) and glycine (1.46 g). The mixture was agitated until the materials dissolved. The pH of the resulting solution was 6.7.

Samples (2 mL each) of this solution were placed in 21 vials with vented rubber stoppers. The vials were lyophilized at −40° C. under vacuum (40-60 mTorr) for about 5 days to give 21 vials containing the monohydrochloride salt (26 mg as free base equivalent), sucrose (26 mg) and glycine (39 mg) as a lyophilized powder.

Analysis of representative vials showed the samples had a water content of 0.5% (Karl Fisher), residual solvent (acetonitrile) of 0.6% (GC analysis) and a purity of 90.4% (HPLC analysis).

C. Dihydrochloride Salt (Formula I, where x is about 2)

Samples (2 mL each) of a salt exchange solution of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]-carbonyl]-26-decarboxyvancomycin dihydrocholoride (124 mL, 13.0 mg/mL) having a pH of 4.4 were placed in 21 vials with vented rubber stoppers. The vials were lyophilized at −40° C. under vacuum (40-60 mTorr) for about 6 days to give 21 vials containing the dihydrochloride salt (26 mg as free base equivalent) as a lyophilized powder.

Analysis of representative vials showed the samples had a water content of 1.1% (Karl Fisher), residual solvent (acetonitrile) of 0.3% (GC analysis) and a purity of 90.1% (HPLC analysis).

D. Dihydrochloride Salt (Formula I, where x is about 2), Sucrose and Glycine

To a salt exchange solution of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin dihydrochloride (150 mL, 13.0 mg/mL, 1.95 g) at pH 4.27 was added sucrose (1.95 g) and the mixture was stirred until the sucrose dissolved. To this solution (104 mL) was added glycine (2.03 g). The mixture was agitated until the glycine dissolved.

Samples (2 mL each) of this solution were placed in 21 vials with vented rubber stoppers. The vials were lyophilized at −40° C. under vacuum (40-60 mTorr) for about 6 days to give 21 vials containing the dihydrochloride salt (26 mg as free base equivalent), sucrose (26 mg) and glycine (39 mg) as a lyophilized powder.

Analysis of representative vials showed the samples had a water content of 0.5% (Karl Fisher), residual solvent (acetonitrile) of 0.8% (GC analysis) and a purity of 90.6% (HPLC analysis).

E. Trihydrochloride Salt (Formula I, where x is about 3)

The pH of a salt exchange solution of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]-carbonyl]-26-decarboxyvancomycin dihydrochloride was adjusted to pH 2.0 by adding 1 N aqueous hydrochloric acid.

Samples (2 mL each) of this solution were placed in 21 vials with vented rubber stoppers. The vials were lyophilized at −40° C. under vacuum (40-60 mTorr) for about 6 days to give 21 vials containing the trihydrochloride salt (26 mg as free base equivalent) as a lyophilized powder.

Analysis of representative vials showed the samples had a water content of <0.8% (Karl Fisher), residual solvent (acetonitrile) of 0.3% (GC analysis) and a purity of 84.5% (HPLC analysis).

F. Trihydrochloride Salt (Formula I, where x is about 3), Sucrose and Glycine

The pH of a solution of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin dihydrochloride (13.0 mg/mL), sucrose (13.0 mg/mL) and glycine (19.5 mg/mL) was adjusted to pH 2.0 by adding dropwise 1 N aqueous hydrochloric acid.

Samples (2 mL each) of this solution were placed in 21 vials with vented rubber stoppers. The vials were lyophilized at −40° C. under vacuum (40-60 mTorr) for about 5 days to give 21 vials containing the trihydrochloride salt (26 mg as free base equivalent), sucrose (26 mg) and glycine (39 mg) as a lyophilized powder.

Analysis of representative vials showed the samples had a water content of 0.5% (Karl Fisher), residual solvent (acetonitrile) of 0.1% (GC analysis) and a purity of 91.3% (HPLC analysis).

Example 13

Storage and Analysis of Stability Samples

Two racks containing six vials of each type of stability sample (Examples 12A-F; 6×6=36 vials) were prepared. One rack was stored protected from light in a drawer at room temperature and the other rack was stored in a refrigerator at 2 to 8° C. A representative vial of each type of stability sample was analyzed by HPLC after storage for 1, 3, 6 and 12 months to determine purity. The results are shown in Tables 1-6.

TABLE 1

Storage Stability of Compounds of Formula I at Refrigerated Temperature

| Time | Monohydrochloride | | Dihydrochloride | | Trihydrochloride | |
|---|---|---|---|---|---|---|
| (M)[1] | Purity (%)[2] | Δ[3] | Purity (%) | Δ | Purity (%) | Δ |
| 0 | 90.4 | — | 90.1 | — | 84.5 | — |
| 1 | 90.0 | −0.4 | 89.9 | −0.2 | 84.0 | −0.5 |
| 3 | 90.2 | −0.2 | 89.4 | −0.7 | 80.7 | −3.8 |
| 6 | 90.4 | 0.0 | 90.8 | 0.7 | 79.4 | −5.1 |
| 12 | 87.4 | −3.0 | 87.2 | −2.9 | 76.0 | −8.6 |

[1]Time in months.
[2]Purity of sample based on HPLC area percent.
[3]Change in percent purity from time = 0.

The data in Table 1 show that the purity of the trihydrochloride salt (formula I, where x is about 3) decreased significantly more than either the mono- or the dihydrochloride salts when the salts were stored at 2 to 8° C. for 12 months. The trihydrochloride salt decreased in purity by 8.6% compared to 3.0% and 2.9% for the mono- and dihydrochloride salts, respectively. These results are shown in FIG. 1.

TABLE 2

Storage Stability of Compounds of Formula I at Room Temperature

| Time | Monohydrochloride | | Dihydrochloride | | Trihydrochloride | |
|---|---|---|---|---|---|---|
| (M)[1] | Purity (%)[2] | Δ[3] | Purity (%) | Δ | Purity (%) | Δ |
| 0 | 90.4 | — | 90.1 | — | 84.5 | — |
| 1 | 89.3 | −1.1 | 85.3 | −4.8 | 74.8 | −9.7 |
| 3 | 82.0 | −8.4 | 82.5 | −7.6 | 69.5 | −15.0 |
| 6 | 79.9 | −10.5 | 81.4 | −8.7 | 56.5 | −28.0 |
| 12 | 67.0 | −23.4 | 69.6 | −20.5 | 50.4 | −34.2 |

[1]Time in months.
[2]Purity of sample based on HPLC area percent.
[3]Change in percent purity from time = 0.

The data in Table 2 show that the purity of the trihydrochloride salt (formula I, where x is about 3) decreased significantly more than either the mono- or the dihydrochloride salt when the salts were stored at room temperature for 12 months. The trihydrochloride salt decreased in purity by 34.2% compared to 23.4% and 20.5% for the mono- and dihydrochloride salts, respectively. These results are shown in FIG. 2.

TABLE 3

Storage Stability of Compounds of Formula I at Refrigerated Temperature in a Composition Containing Sucrose and Glycine

| Time | Monohydrochloride | | Dihydrochloride | | Trihydrochloride | |
|---|---|---|---|---|---|---|
| (M)[1] | Purity (%)[2] | Δ[3] | Purity (%) | Δ | Purity (%) | Δ |
| 0 | 90.4 | — | 90.6 | — | 91.3 | — |
| 1 | 90.7 | 0.3 | 89.8 | −0.3 | 91.5 | 0.2 |
| 3 | 88.9 | −1.5 | 89.4 | −0.7 | 90.8 | −0.5 |
| 6 | 91.7 | 1.3 | 90.8 | 0.7 | 92.8 | 1.5 |
| 12 | 88.5 | −1.9 | 87.2 | −2.9 | 90.1 | −1.2 |

[1]Time in months.
[2]Purity of sample based on HPLC area percent.
[3]Change in percent purity from time = 0.

The data in Table 3 show that the purity of the mono-, di- and trihydrochloride salts (formula I, where x is about 1, 2 and 3, respectively) decreased by a similar percent when the salts were formulated with sucrose and glycine and stored at 2 to 8° C. for 12 months. The mono-, di- and trihydrochloride salts decreased in purity by 1.9%, 2.9% and 1.2%, respectively.

TABLE 4

Storage Stability of Compounds of Formula I at Room Temperature in a Composition Containing Sucrose and Glycine

| Time | Monohydrochloride | | Dihydrochloride | | Trihydrochloride | |
|---|---|---|---|---|---|---|
| (M)[1] | Purity (%)[2] | Δ[3] | Purity (%) | Δ | Purity (%) | Δ |
| 0 | 90.4 | — | 90.6 | — | 91.3 | — |
| 1 | 89.0 | −1.4 | 89.8 | −0.8 | 89.2 | −2.1 |
| 3 | 86.9 | −3.5 | 87.7 | −2.9 | 84.4 | −6.9 |
| 6 | 87.9 | −2.5 | 90.8 | 0.2 | 82.5 | −8.8 |
| 12 | 81.5 | −8.9 | 83.8 | −6.8 | 65.0 | −26.3 |

[1]Time in months.
[2]Purity of sample based on HPLC area percent.
[3]Change in percent purity from time = 0.

Figure 3:
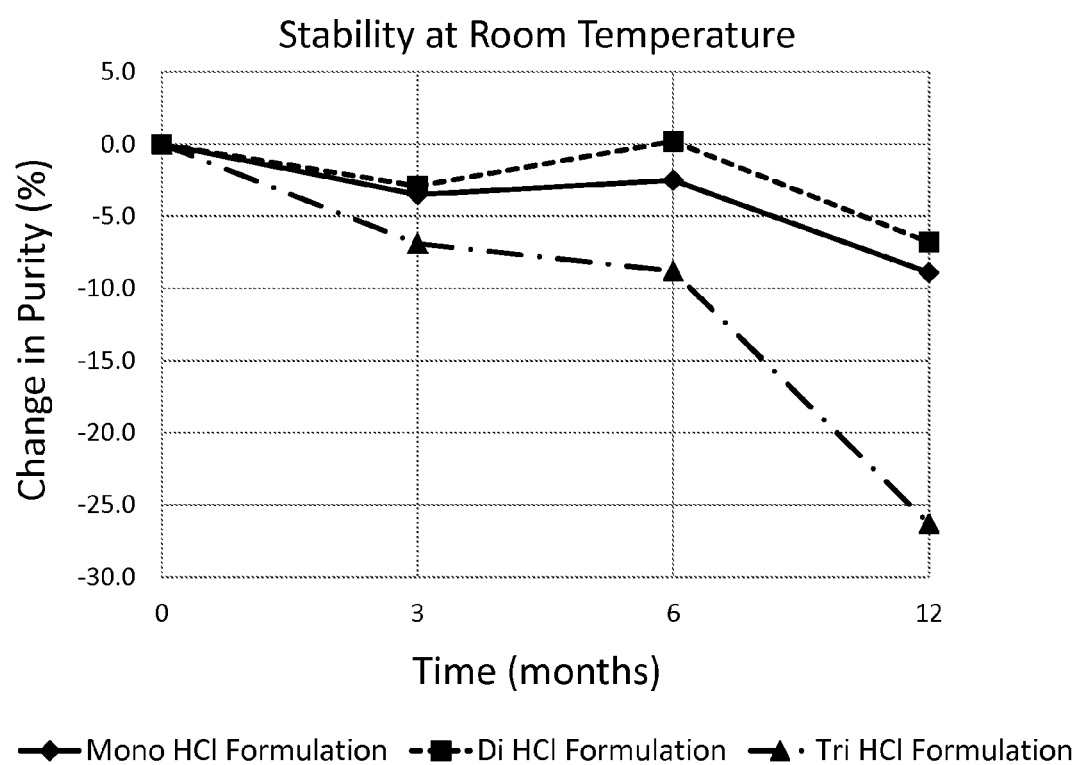
FIG. 3 shows the change in purity (percent) versus time (months) for compositions containing (a) a mono-, di- or trihydrochloride salts of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]-carbonyl]-26-decarboxyvancomycin; (b) sucrose; and (c) glycine; where the composition has been stored at room temperature.

The data in Table 4 show that the purity of the trihydrochloride salt (formula I, where x is about 3) decreased significantly more than either the mono- or the dihydrochloride salt when the salts were formulated with sucrose and glycine and stored at room temperature for 12 months. The trihydrochloride salt decreased in purity by 26.3% compared to 8.9% and 6.8% for the mono- and dihydrochloride salts, respectively. These results are shown in FIG. 3.

TABLE 5

Storage Stability of the Monohydrochloride Salt (Formula I, where x is about 1) at Room Temperature

| Time | Mono HCl | | Mono HCl + Sucrose + Glycine | |
|---|---|---|---|---|
| (M)[1] | Purity (%)[2] | Δ[3] | Purity (%) | Δ |
| 0 | 90.4 | — | 90.4 | — |
| 1 | 89.3 | −1.1 | 89.0 | −1.4 |
| 3 | 82.0 | −8.4 | 86.9 | −3.5 |

TABLE 5-continued

Storage Stability of the Monohydrochloride Salt
(Formula I, where x is about 1) at Room Temperature

| Time | Mono HCl | | Mono HCl + Sucrose + Glycine | |
|---|---|---|---|---|
| (M)[1] | Purity (%)[2] | Δ[3] | Purity (%) | Δ |
| 6 | 79.9 | −10.5 | 87.9 | −2.5 |
| 12 | 67.0 | −23.4 | 81.5 | −8.9 |

[1]Time in months.
[2]Purity of sample based on HPLC area percent.
[3]Change in percent purity from time = 0.

Figure 4:
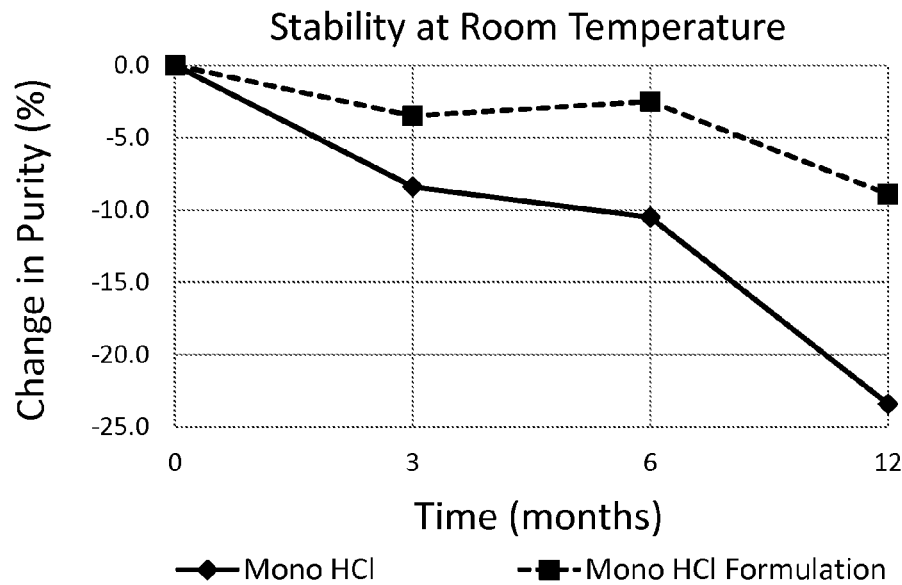
FIG. 4 shows the change in purity (percent) versus time (months) for the monohydrochloride salt of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin and a composition containing (a) the monohydrochloride salt; (b) sucrose; and (c) glycine; where the monohydrochloride salt and the composition have been stored at room temperature.

The data in Table 5 show that the purity of the monohydrochloride salt (formula I, where x is about 1) decreased significantly less when the salt was formulated with sucrose and glycine and stored at room temperature for 12 months. The monohydrochloride salt decreased in purity by 23.4% compared to 8.9% for the monohydrochloride formulated with sucrose and glycine. These results are shown in FIG. 4.

TABLE 6

Storage Stability of the Dihydrochloride Salt
(Formula I, where x is about 2) at Room Temperature

| Time | Di HCl | | Di HCl + Sucrose + Glycine | |
|---|---|---|---|---|
| (M)[1] | Purity (%)[2] | Δ[3] | Purity (%) | Δ |
| 0 | 90.1 | — | 90.6 | — |
| 1 | 85.3 | −4.8 | 89.8 | −0.8 |
| 3 | 82.5 | −7.6 | 87.7 | −2.9 |
| 6 | 81.4 | −8.7 | 90.8 | 0.2 |
| 12 | 69.6 | −20.5 | 83.8 | −6.8 |

[1]Time in months.
[2]Purity of sample based on HPLC area percent.
[3]Change in percent purity from time = 0.

Figure 5:
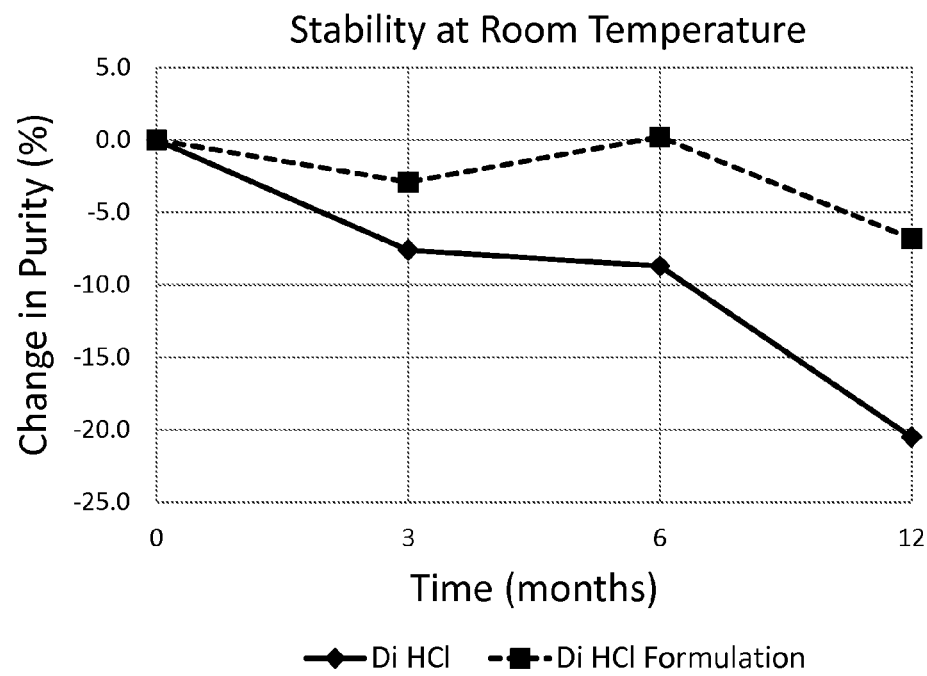
FIG. 5 shows the change in purity (percent) versus time (months) for the dihydrochloride salt of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]carbonyl]-26-decarboxyvancomycin and a composition containing (a) the dihydrochloride salt; (b) sucrose; and (c) glycine; where the dihydrochloride salt and the composition have been stored at room temperature.

The data in Table 6 show that the purity of the dihydrochloride salt (formula I, where x is about 2) decreased significantly less when the salt was formulated with sucrose and glycine and stored at room temperature for 12 months. The dihydrochloride salt decreased in purity by 20.5% compared to 6.8% for the dihydrochloride formulated with sucrose and glycine. These results are shown in FIG. 5.

In summary, compounds of formula I, where x is about 1 and about 2, i.e., the mono- and dihydrochloride salts, are significantly more stable than the trihydrochloride salt when the salts are stored for 12 months at either room temperature or 2 to 8° C. Additionally, the mono- and dihydrochloride salts are more stable when stored at room temperature for 12 months when such salts are formulated with sucrose and glycine.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:
1. A compound of formula I:

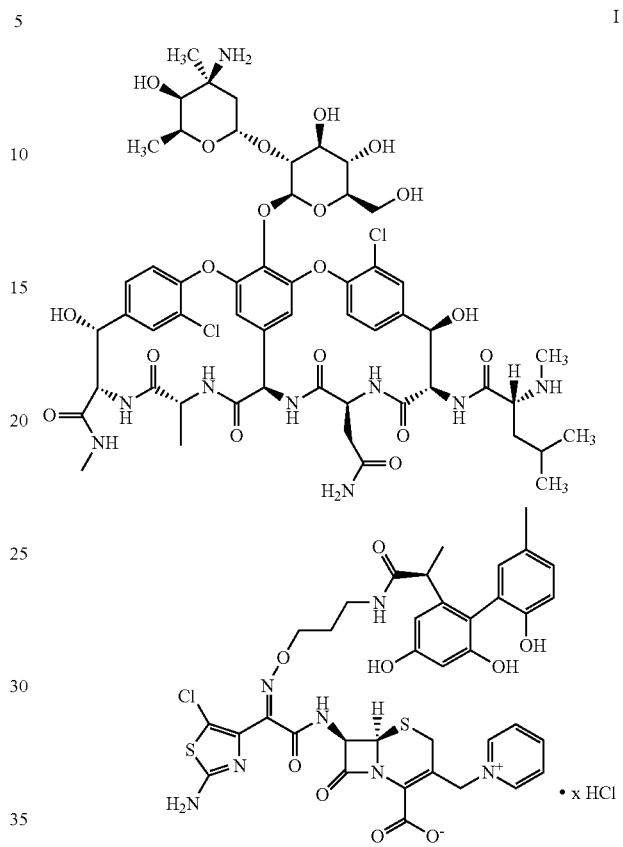

wherein x is in the range of from 1 to 2.

2. The compound of claim 1, wherein x is 1.
3. The compound of claim 1, wherein x is 2.
4. A pharmaceutical composition comprising a pharmaceutically acceptable carrier and a compound of claim 1, 2 or 3.
5. A pharmaceutical composition comprising (a) a compound of claim 1, 2 or 3; (b) sucrose and (c) glycine or a pharmaceutically-acceptable salt thereof.
6. The pharmaceutical composition of claim 5, wherein the composition is a lyophilized composition.
7. A pharmaceutical composition comprising:
   (a) a compound of claim 1, 2 or 3;
   (b) 0.5 to 2.0 parts by weight of sucrose; and
   (c) 0.5 to 2.0 parts by weight of glycine (as the free base equivalent); wherein the parts by weight of sucrose and glycine are based on the part by weight of the compound of claim 1, 2 or 3 (as the free base equivalent).
8. The pharmaceutical composition of claim 6, wherein the composition comprises 1.0 part by weight of sucrose; and 1.5 parts by weight of glycine.
9. A process for preparing a compound of claim 1, the process comprising the steps of:
   (a) forming an aqueous composition comprising 26-[[[3-[[(Z)-[1-(2-amino-5-chloro-4-thiazolyl)-2-[[[(6R,7R)-2-carboxy-8-oxo-3-(pyridiniomethyl)-5-thia-1-azabicyclo[4.2.0]oct-2-en-7-yl]amino]-2-oxoethylidene]amino]oxy]propyl]amino]-carbonyl]-26-decarboxyvancomycin and hydrochloric acid in a molar ratio of about 1:1 to about 1:2;

(b) lyophilizing the aqueous composition to provide a compound of claim 1.

10. The process of claim 9, wherein the molar ratio is about 1:1.

11. The process of claim 9, wherein the molar ratio is about 1:2.

12. A method for reducing the degradation of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]-amino]oxy]propyl]amino]-carbonyl]-26-decarboxyvancomycin during storage, the method comprising (a) forming a compound of claim 1, 2 or 3 and (b) storing the compound of claim 1, 2 or 3 at a temperature in the range of from about −25° C. to about 25° C.

13. The method of claim 12, wherein the temperature is in the range of from about 2° C. to about 8° C.

14. A method for reducing the degradation of 26-[[[3-[[(Z)-[1-(2-amino-5-chloro-4-thiazolyl)-2-[[(6R,7R)-2-carboxy-8-oxo-3-(pyridiniomethyl)-5-thia-1-azabicyclo[4.2.0]oct-2-en-7-yl]amino]-2-oxoethylidene]-amino]oxy]propyl]amino]-carbonyl]-26-decarboxyvancomycin during storage, the method comprising (a) forming a pharmaceutical composition of claim 8 and (b) storing the pharmaceutical composition at a temperature in the range of from about −25° C. to about 25° C.

15. The method of claim 14, wherein the temperature is in the range of from about 2° C. to about 8° C.

* * * * *

UNITED STATES PATENT AND TRADEMARK OFFICE
CERTIFICATE OF CORRECTION

PATENT NO. : 9,161,990 B2  
APPLICATION NO. : 14/198956  
DATED : October 20, 2015  
INVENTOR(S) : Weijiang Zhang et al.

Page 1 of 1

It is certified that error appears in the above-identified patent and that said Letters Patent is hereby corrected as shown below:

On the title page of the patent, item (54), the title should read

HYDROCHLORIDE SALTS OF A GLYCOPEPTIDE-CEPHALOSPORIN ANTIBIOTIC COMPOUND

On page 2, line 14, in item (56), under Foreign Patent Documents,

"JP 03/031449 A" should be "JP 2010105965 A"

Signed and Sealed this  
Fifth Day of April, 2016

Michelle K. Lee  
*Director of the United States Patent and Trademark Office*